United States Patent
Carman et al.

(10) Patent No.: US 9,730,783 B2
(45) Date of Patent: Aug. 15, 2017

(54) ULTRA-LOW FRACTIONAL AREA COVERAGE FLOW DIVERTER FOR TREATING ANEURYSMS AND VASCULAR DISEASES

(71) Applicant: THE REGENTS OF THE UNIVERSITY OF CALIFORNIA, Oakland, CA (US)

(72) Inventors: Gregory P. Carman, Los Angeles, CA (US); Daniel S. Levi, Pacific Palisades, CA (US); Youngjae Chun, Pittsburgh, PA (US); Fernando Vinuela, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 184 days.

(21) Appl. No.: 13/668,241

(22) Filed: Nov. 3, 2012

(65) Prior Publication Data
US 2014/0249620 A1    Sep. 4, 2014

Related U.S. Application Data

(63) Continuation of application No. PCT/US2011/037988, filed on May 25, 2011.
(Continued)

(51) Int. Cl.
*A61F 2/06* (2013.01)
*A61F 2/01* (2006.01)
(Continued)

(52) U.S. Cl.
CPC ............. *A61F 2/07* (2013.01); *A61F 2/90* (2013.01); *A61L 31/022* (2013.01); *A61L 31/14* (2013.01);
(Continued)

(58) Field of Classification Search
CPC .......... A61F 2/07; A61F 2/90; A61F 2002/068
(Continued)

(56) References Cited

U.S. PATENT DOCUMENTS 3,798,061 A    3/1974  Yamazaki
6,096,175 A    8/2000  Roth
(Continued)

FOREIGN PATENT DOCUMENTS

WO    WO 2006/034114 A2    3/2006
WO    WO 2007/051179 A2    5/2007
(Continued)

OTHER PUBLICATIONS

Sergueeva et al.; Structure and properties of amorphous and nanocrystalline NiTi prepared by severe plastic deformation and annealing; Materials Science and Engineering A339; 2003; p. 159-165.*
(Continued)

*Primary Examiner* — David Isabella
*Assistant Examiner* — Dinah Baria
(74) *Attorney, Agent, or Firm* — Morgan, Lewis & Bockius LLP

(57) ABSTRACT

A flow diverter is described and fabricated using ultra-thin porous thin-film Nitinol, and is configured for implantation to a treatment site within a vessel for significant reduction in an intra-aneurismal flow velocity and vorticity. Using small size pores in a coverage area of only 10%, a 90% reduction in flow velocity into a pseudo-aneurysm can be achieved, with an almost immediate cessation of flow into an anatomical feature such as aneurysm sac in vivo. The size of the holes can be tailored to be any shape and range in size from 1-400 μm using photolithography and from 5-1000 nm using ebeam lithography.

17 Claims, 20 Drawing Sheets

Related U.S. Application Data

(60) Provisional application No. 61/348,239, filed on May 25, 2010.

(51) Int. Cl.

| | | |
|---|---|---|
| *A61F 2/07* | (2013.01) | |
| *A61F 2/90* | (2013.01) | |
| *A61L 31/02* | (2006.01) | |
| *A61L 31/14* | (2006.01) | |
| *C23C 14/00* | (2006.01) | |
| *C23C 14/18* | (2006.01) | |
| *C23C 14/58* | (2006.01) | |
| *C23C 14/34* | (2006.01) | |
| *A61F 2/82* | (2013.01) | |

(52) U.S. Cl.
CPC ........ *C23C 14/0005* (2013.01); *C23C 14/185* (2013.01); *C23C 14/34* (2013.01); *C23C 14/5806* (2013.01); *C23C 14/5873* (2013.01); *A61F 2002/068* (2013.01); *A61F 2002/075* (2013.01); *A61F 2002/077* (2013.01); *A61F 2002/823* (2013.01); *A61F 2230/0054* (2013.01)

(58) Field of Classification Search
USPC ........................................ 623/1.1, 1.13, 1.39
See application file for complete search history.

(56) References Cited

U.S. PATENT DOCUMENTS

| | | | |
|---|---|---|---|
| 6,120,535 A | 9/2000 | McDonald et al. | |
| 6,120,917 A | 9/2000 | Eda | |
| 6,245,102 B1 | 6/2001 | Jayaraman | |
| 6,435,660 B1 | 8/2002 | Ozaki et al. | |
| 6,540,849 B2 * | 4/2003 | DiCarlo et al. | 148/402 |
| 6,790,372 B2 * | 9/2004 | Roy | A61M 37/0015 216/10 |
| 7,704,274 B2 | 4/2010 | Boyle et al. | |
| 8,313,523 B2 | 11/2012 | Banas et al. | |
| 8,690,938 B2 | 4/2014 | Tenne | |
| 2001/0039449 A1 | 11/2001 | Johnson et al. | |
| 2002/0165600 A1 | 11/2002 | Banas et al. | |
| 2003/0060782 A1 | 3/2003 | Bose et al. | |
| 2003/0100945 A1 | 5/2003 | Yodfat et al. | |
| 2003/0132193 A1 | 7/2003 | Okamoto | |
| 2004/0169007 A1 | 9/2004 | Sander et al. | |
| 2005/0033418 A1 | 2/2005 | Banas et al. | |
| 2005/0186241 A1 | 8/2005 | Boyle et al. | |
| 2005/0283220 A1 | 12/2005 | Gobran et al. | |
| 2006/0142845 A1 | 6/2006 | Molaei et al. | |
| 2006/0259131 A1 | 11/2006 | Molaei et al. | |
| 2007/0073374 A1 | 3/2007 | Anderl et al. | |
| 2007/0225800 A1 | 9/2007 | Sahatjian et al. | |
| 2008/0004691 A1 * | 1/2008 | Weber et al. | 623/1.16 |
| 2008/0203012 A1 | 8/2008 | Yeager et al. | |
| 2010/0298515 A1 * | 11/2010 | Marchand et al. | 526/336 |
| 2014/0249620 A1 | 9/2014 | Carman et al. | |

FOREIGN PATENT DOCUMENTS

| | | | | |
|---|---|---|---|---|
| WO | WO 2008/151204 | * | 12/2008 | A61F 2/06 |
| WO | WO2008/151204 A1 | | 12/2008 | |
| WO | 2010/102254 A2 | | 9/2010 | |

OTHER PUBLICATIONS

Tateshima et al., "Alteration of intraaneurysmal hemodynamis by placement of a self-expandable stent," J Neurosurg, 111, Mar. 6, 2009, pp. 22-27.
Korean Intellectual Property Office, International Search Report and Written Opinion (pp. 1-14) issued on Feb. 9, 2012 for corresponding International Patent Application No. PCT/US2011/037988 and claims searched (pp. 15-20) pp. 1-20.
Chun, Y.J., et al. "Novel micro-patterning processes for thin film NiTi vascular devices," Smart Mater. Struct. Aug. 25, 2010, pp. 105021-10530.
Chu, C.L., et al., "Surface oxidation of NiTi shape memory alloy in a boiling aqueous solution containing hydrogen peroxide," Materials Science and Engineering 417(2006), pp. 104-109.
Augsburger, L., et al., "Effect of flow diverter porosity on intraaneurysmal blood flow," Clin Neuroradiol, 3, (2009), pp. 204-214.
International Search Report and Written Opinion, PCT/US2010026430, Nov. 26, 2010, 23 pgs.
Levi, Office Action, U.S. Appl. No. 13/224,103, Jul. 28, 2015, 38 pgs.
Levi, Final Office Action, U.S. Appl. No. 13/224,103, Feb. 19, 2016, 39 pgs.
The Regents of the University of California, Communication Pursuant to Article 94(3) EPC, EP10749417.1, Jul. 3, 2015, 4 pgs.
The Regents of the University of California, Decision to Grant, EP10749417.1, Jun. 23, 2016, 1 pg.
The Regents of the University of California Office Action, app No. CA 2,753,853, Jan. 29, 2016, 6 pgs.
Notice of Grant, Patent Certificate, EP10749417.1, Jul. 20, 2016, 1 pg.

* cited by examiner

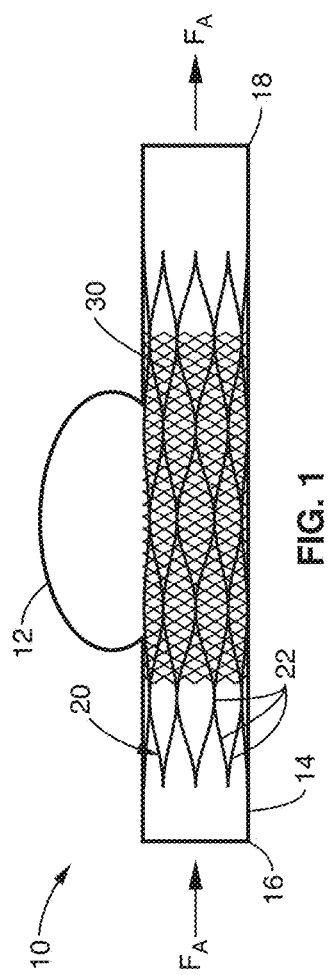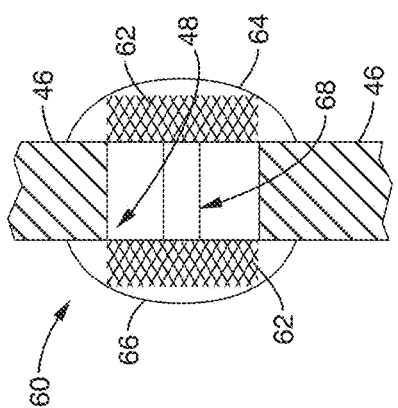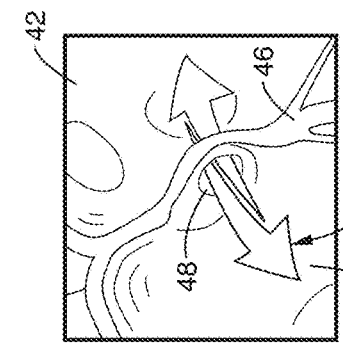

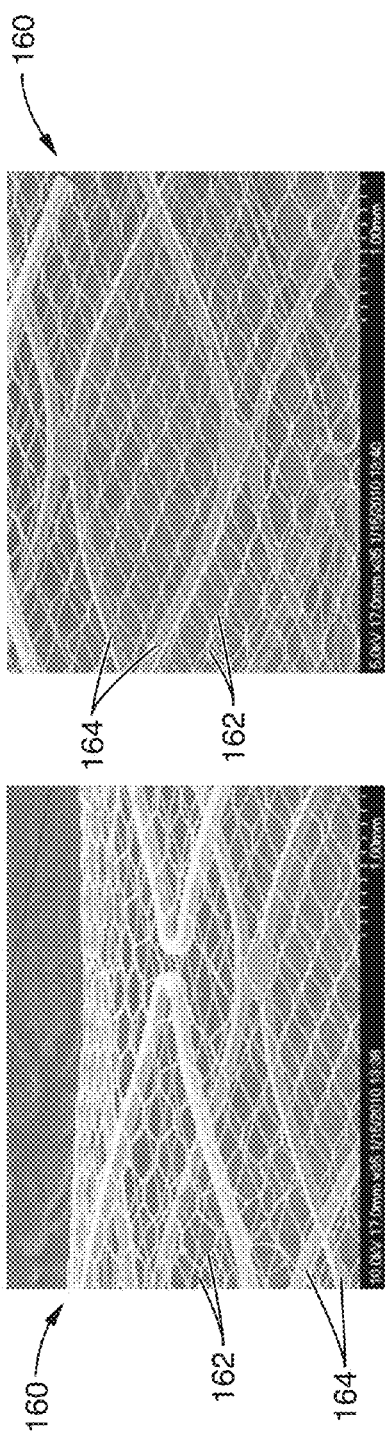
FIG. 10A
FIG. 10B
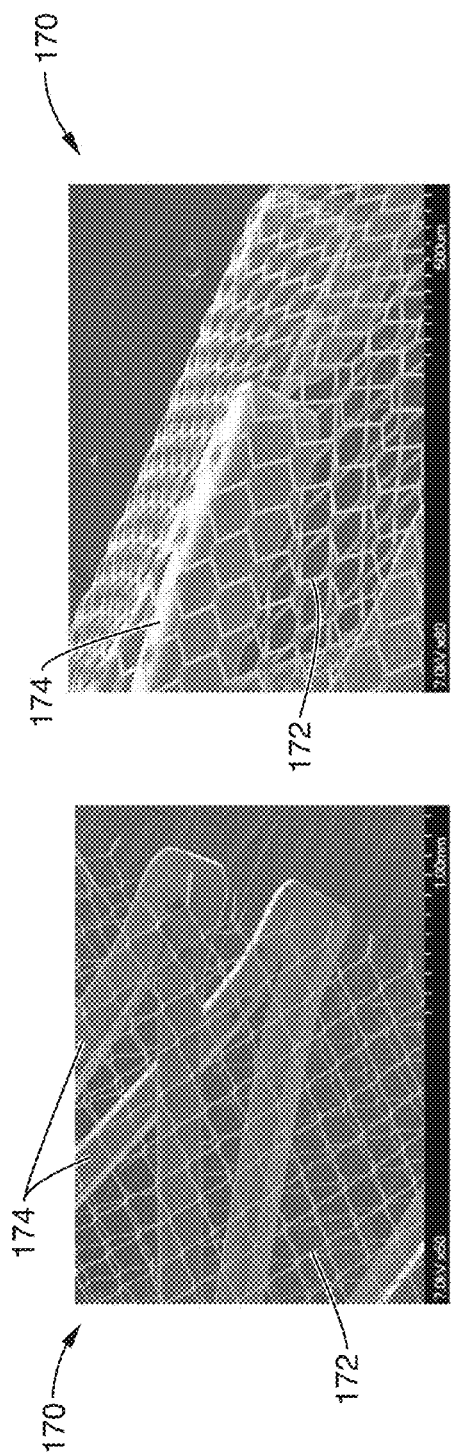
FIG. 11A
FIG. 11B

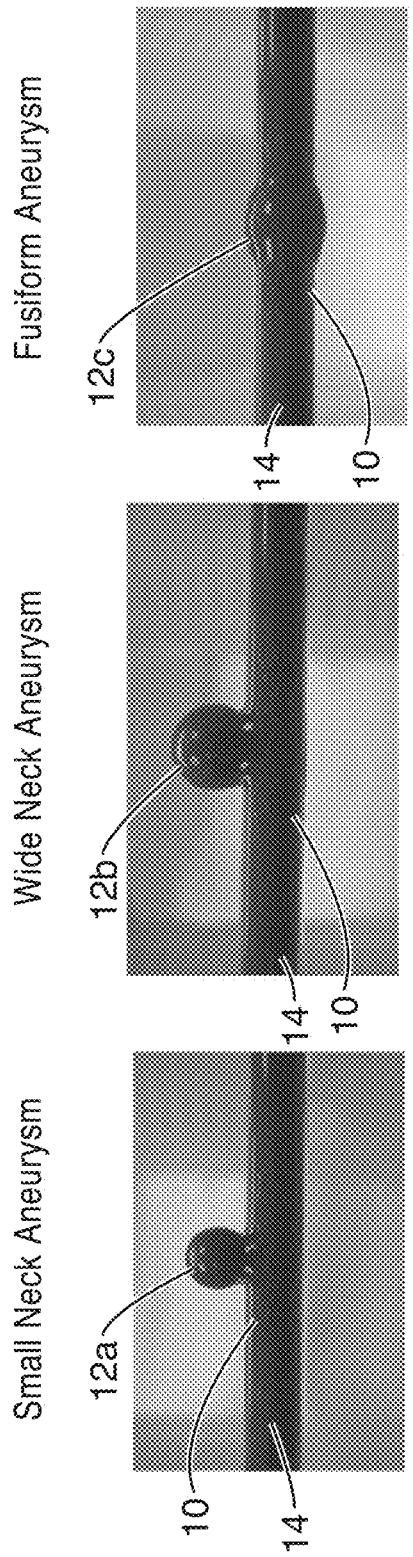

300μm Patterned Thin Film NiTi 4.5mm Diameter Wingspan Stent

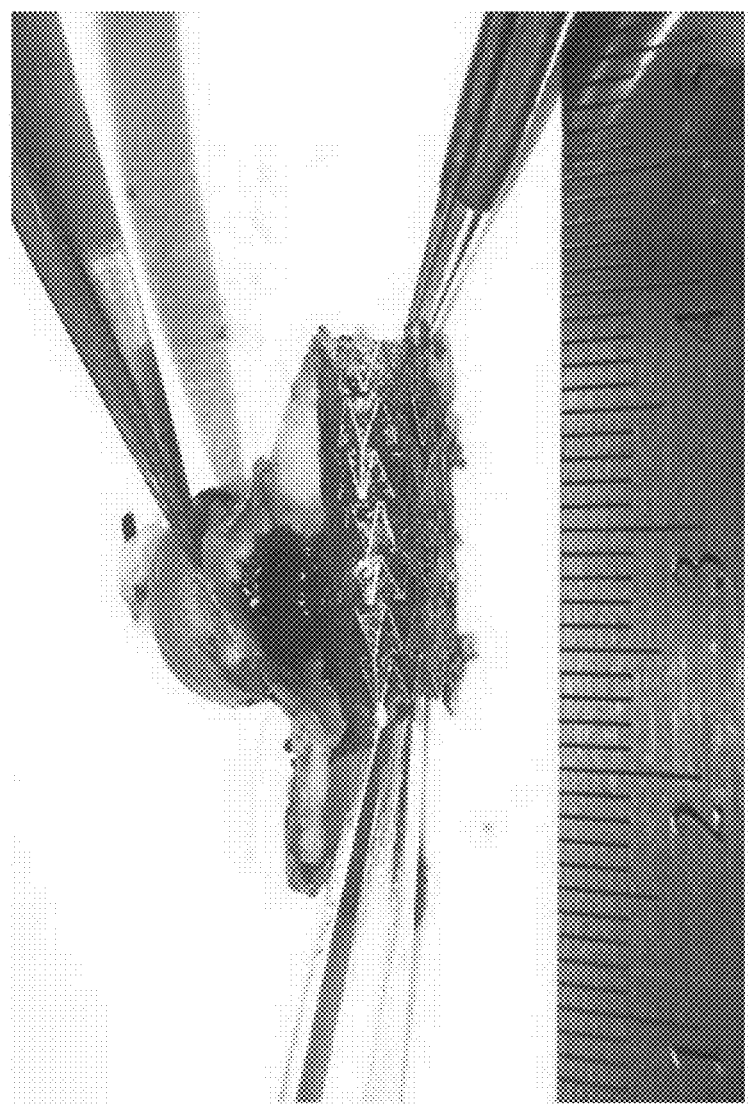

ULTRA-LOW FRACTIONAL AREA COVERAGE FLOW DIVERTER FOR TREATING ANEURYSMS AND VASCULAR DISEASES

CROSS-REFERENCE TO RELATED APPLICATIONS

This application is a 35 U.S.C. §111(a) continuation of PCT international application number PCT/US2011/037988 filed on May 25, 2011, incorporated herein by reference in its entirety, which is a nonprovisional of U.S. provisional patent application No. 61/348,239, filed on May 25, 2010, incorporated herein by reference in its entirety. Priority is claimed to each of the foregoing applications.

The above-referenced PCT international application was published as PCT International Publication No. WO 2011/150118 on Dec. 1, 2011 and republished on Apr. 5, 2012, and is incorporated herein by reference in its entirety.

This application is related to PCT International Application No. PCT/US2010/026430 filed on Mar. 5, 2010, published on Sep. 10, 2010 as PCT International Publication No. WO 2010/102254, and republished on Jan. 20, 2011, incorporated herein by reference in its entirety.

STATEMENT REGARDING FEDERALLY SPONSORED RESEARCH OR DEVELOPMENT

This invention was made with Government support under Grant No. W81XWH-07-1-0672, awarded by the ARMY/Medical Research and Materiel Command. The Government has certain rights in this invention.

INCORPORATION-BY-REFERENCE OF MATERIAL SUBMITTED ON A COMPACT DISC

Not Applicable

BACKGROUND OF THE INVENTION

1. Field of the Invention

This invention pertains generally to flow diverters, and more particularly to thin-film flow diverters for treatment of vascular diseases.

2. Description of Related Art

Conventional stent structures do not provide sufficient flow diversion to treat aneurysms. Ultra-low porous graft membrane such as ePTFE or Dacron polyester are too bulky and thrombogenic to be appropriate for use in the treatment of aneurysms in small vessels (e.g. vessels less than 5 mm in diameter, including neurovascular and peripheral arterial circulation) but have been successful in flow diversion in larger vessels (e.g. abdominal and thoracic aortic aneurysms).

PTFE, Dacron and other polymer structures are fabricated in such a fashion that it is extremely difficult to precisely control the porosity to a tolerance of 1 micron. Even in cases where porosity can macroscopically be controlled in these materials, specific shapes and distributions cannot be generated precisely. For example, it is highly difficult, if not impossible, to specifically fabricate a circular or diamond shape pattern that is regular and repeating into structures comprising these materials. In addition, ePTFE and Dacron are also very thick relative to thin films (on the order of 100 microns thick). This increases the size of any flow diversion device without providing significant benefit in regards to the thickness direction.

In many flow diverter applications, complete occlusion of the vessel's anomaly is unnecessary, and only partial occlusion is generally desired or warranted. Previous teachings of using deployable stents indicate for neurovascular applications the coverage area of the aneurysm sac must be at least 30%. These studies use large size holes (relative to the dimension of blood products) for evaluation.

Current approaches to prevent aneurysms from rupturing include both surgical and transcatheter methods. A surgical approach to treat aneurysms by "clipping" the aneurysm neck was developed by Dandy in 1936 and proved to be an effective treatment for a select group of aneurysms. However, this procedure requires a craniotomy (an opening in the skull) and is not always applicable depending on the aneurysm size, location, and complexity.

More recently, transcatheter procedures to treat vascular aneurysms have been developed. An endovascular therapy using platinum coils to fill the aneurysm sac was introduced in 1990. Because this coil embolization technique is less invasive and more cost effective than surgery, it has become the standard of care for most aneurysms. These coils pack the aneurysm sac densely to limit blood flow in the aneurysm and produce more local thrombosis within the aneurysm. While coils are beneficial, they can only be used for aneurysms with "necks" narrow enough to hold coils in the aneurysm. To address this issue, a stent can be placed across the neck of a broad-neck aneurysm and coils placed into the aneurysm through the cells of the stent. This procedure is complicated (it involves two types of devices: a stent and multiple coils), sometimes does not produce aneurysm occlusion, and is limited by the physical size of the stent's delivery system. The ideal device for treatment of aneurysms would be a "covered" stent, which occludes the neck of both narrow and broad necked aneurysms.

"Covered stents" have traditionally been conventional mesh type stents wrapped in expanded polytetrafluoroethylene (ePTFE). While they can wall off aneurysms by circumferentially covering the wall of an artery, they have been far too bulky for use as neurovascular stents or in other flow diversion vascular systems requiring a low profile. A low profile covered stent for the treatment of aneurysms in small, tortuous vessels has yet to be fully evaluated in vivo or in vitro.

Therefore, an object of the present invention is production and use of a thin-film structure (e.g. 1-10 microns) that can be patterned with specific shapes with a relatively high tolerance level (e.g. 1 micron or less).

Another object is to decrease the percent coverage of the material deployed over an aneurism sac by reducing the size of the fenestration.

A further object is a thin-film manufacturing process to enable a wide range of different shapes and distributions to be manufactured onto a single vascular flow diverter.

Another object is to provide a surface treatment to the thin-film that produces a rapid clotting cascade preventing flow into the aneurysm sac. At least some of these objectives will be met in the description provided below.

BRIEF SUMMARY OF THE INVENTION

An aspect of the present invention is patterning of thin films, and in particular construction of vascular flow diversion devices for various vascular diseases including but not limited to treating aneurysms and other applications. The devices of the present invention are configured to be extremely low profile and are covered with the minimal amount of blood contacting material. The thin-film manufacturing processes of the present invention allow for production of ultra-low profile and hyperelastic structures (e.g. >400% elongation). These hyperelastic properties allows for the creation of self expanding vascular flow diversion devices, and in particular delivery of the material on a self expanding platform without folding of the material. In vitro and in vivo experiments show flow diversion devices manufactured with the micro-machined thin-film of the present invention, along with a stent or support structure, do not generate thrombosis in the arteries less than 5 mm and provide adequate and rapid flow diversion without production of intimal hyperplasia or vascular stenosis.

Simulated blood studies have shown that the thin-film structures of the present invention are capable of reducing the intra-aneurismal flow velocity and vorticity greater than 90% in a pseudo-aneurysm, even though the coverage area was less than ~10%.

In-vitro flow studies of the thin-film structures of the present invention using human whole blood shows an occlusion of a pseudo-aneurism within approximately 15-30 minutes using a 200 micron fenestration (i.e. 300 micron as fabricated). Occlusion occurred due to the deposition of blood products such as fibrin scaffolds on the mesh structure.

In animal studies, micro-machined thin-film flow diverters with 200 microns fenestrations (i.e. 300 microns as fabricated) were demonstrated to occlude surgically created aneurysms in less than 5 minutes. Flow diversion devices with 400 micron fenestrations (i.e. 500 microns as fabricated) occluded broad necked aneurysm within less than an hour.

Given the overall porosity and sparse coverage (~10% coverage), the rapid flow diversion seen with the devices of the present invention in the lab and in animals represents a paradigm shift in future flow diverter technology. The physical size of the fenestration and surface treatment are of utmost importance, even with low density of coverage. General convention in the existing art is that is would not be possible to so quickly occlude an aneurysm sac without using a more complete covering (e.g. >40-50% coverage).

Test results show that the size of the fenestration (e.g. 200 micron size and 300 micron as fabricated) as well as surface treatment may be critical for proper function within a particular size vessel and flow conditions. Depending on the application (e.g. the size and flow dynamics of the parent artery), fenestrations in a particular range will immediately produce the formation of fibrin structures due to the flow disruptions imposed by the ultra-fine size fenestrations. Such an affect has not been previously shown nor contemplated by those skilled in the art. While the systems and methods of the present invention present a major breakthrough for treating brain aneurysms, the methods and systems of the present invention may be configured for use in a wide range of applications where flow diversion is desired.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1 shows a schematic diagram of ultra-low profile micropatterned thin-film Nitinol flow diverter placed in the small/broad-neck aneurysm site.

FIG. 2 illustrates a heart having an Atrial Septal Defect (ASD).

FIG. 3 shows a flow diverter assembly installed in a location within a patient's heart to treat an Atrial Septal Defect (ASD).

FIGS. 10A and 10B show two views of a flow diverter comprising a hyper-elastic, high-porous thin film disposed over a Neuroform stent.

FIGS. 11A and 11B show two views of a flow diverter comprising a hyper-elastic, high-porous thin-film disposed over a pfm stent.

Figure 13A:
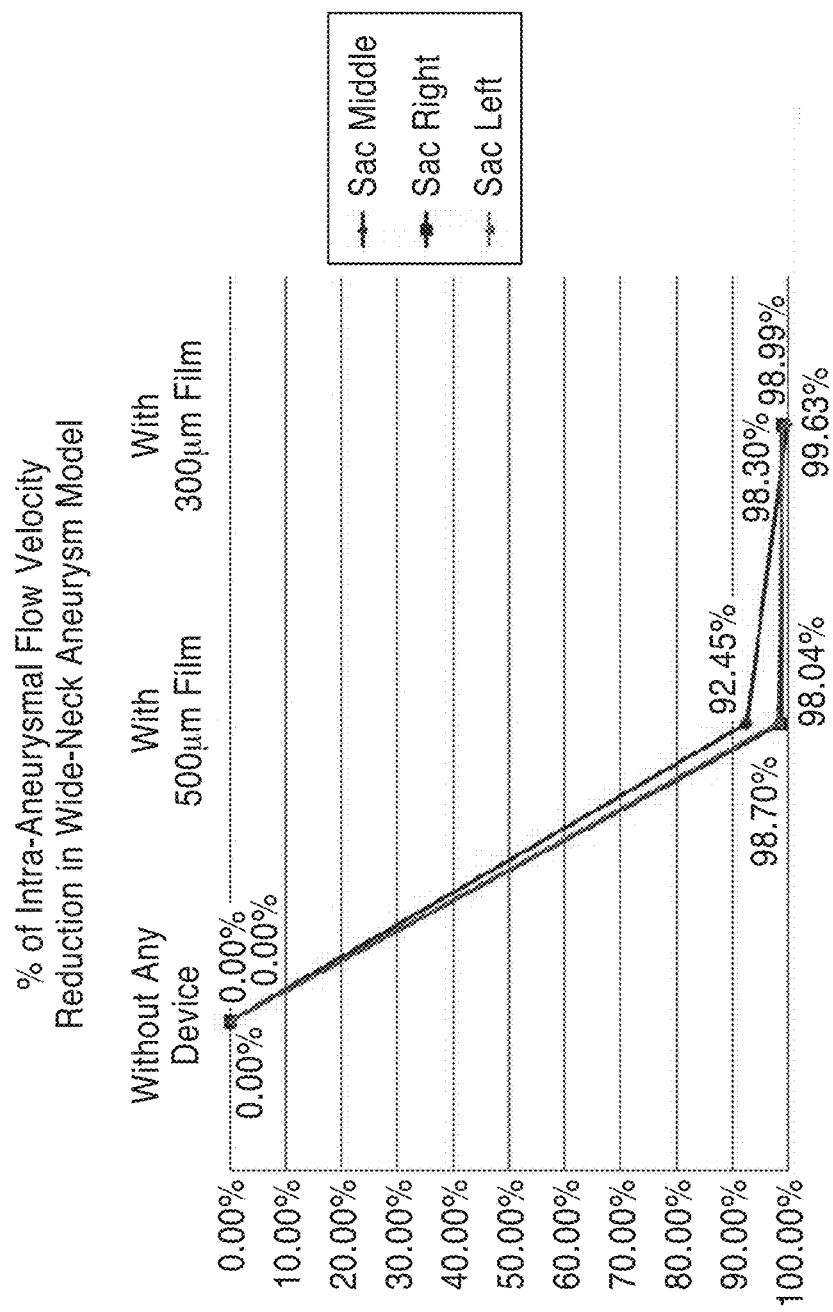
Figure 13B:
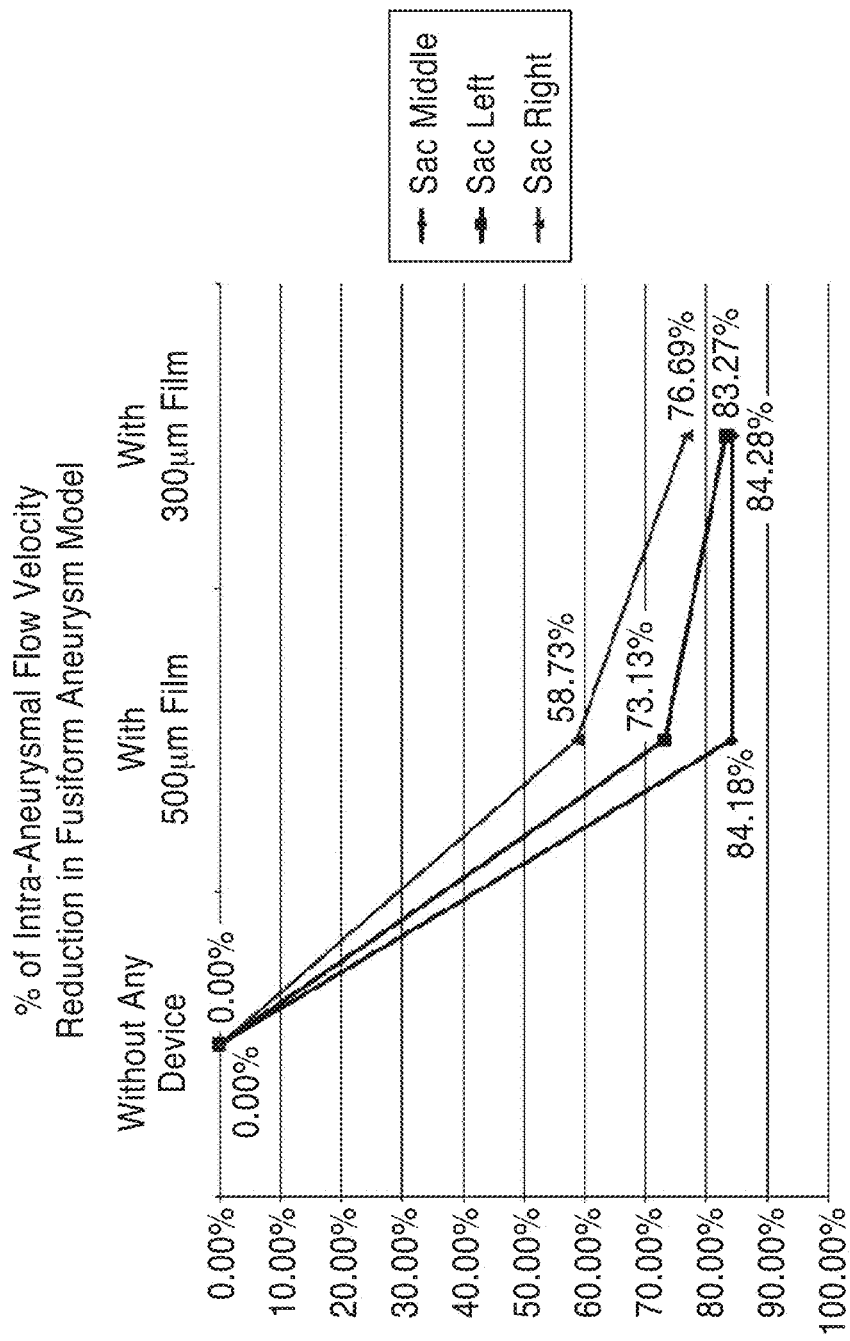

FIGS. 13A and 13B show plots of interaneurismal flow. FIG. 13A shows the percent reduction in flow velocity in wide neck aneurysm sac. FIG. 13B shows the percent reduction in flow velocity in fusiform aneurysm.

FIGS. 14A through 14C show flow diverters of the present invention installed within different aneurism types (small neck: FIG. 14A; wide neck: FIG. 14B; and fusiform: FIG. 14C) of in vitro models with human whole blood.

Figure 15B:
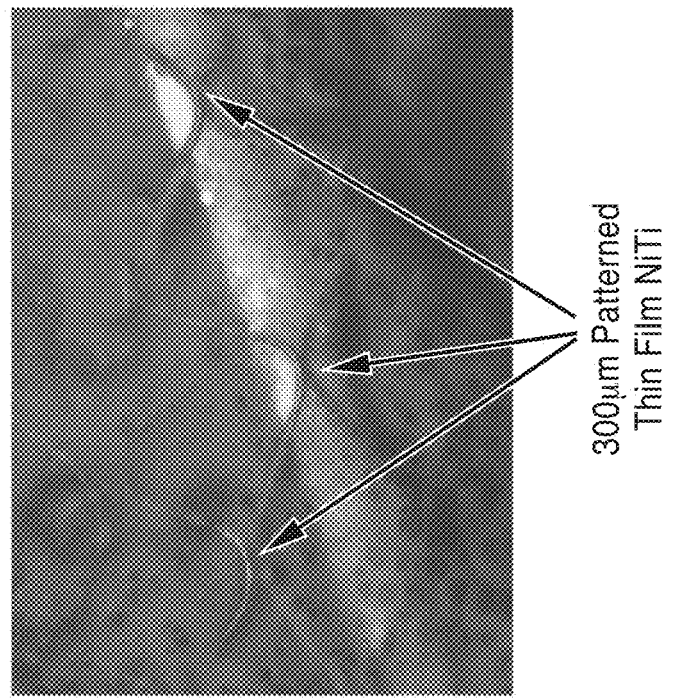
Figure 15A:
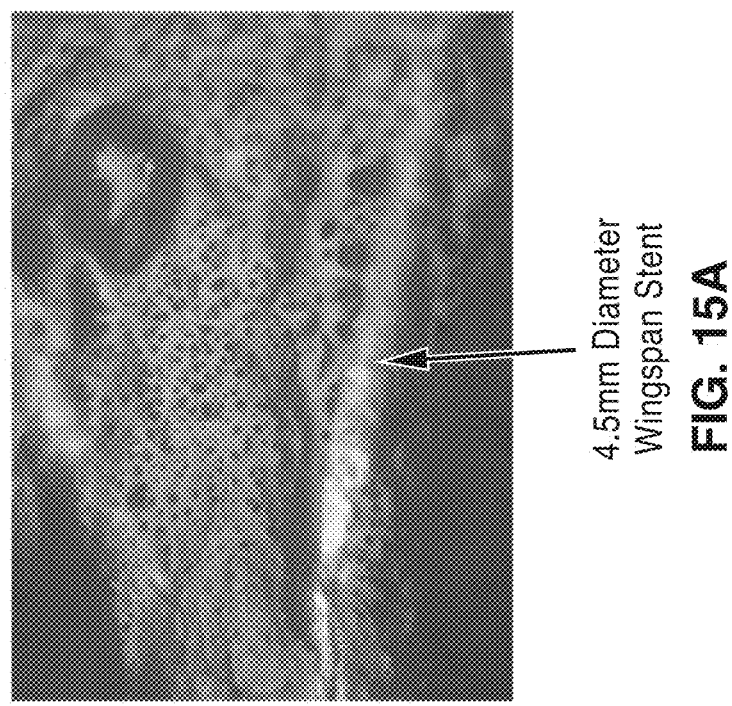

FIGS. 15A and 15B show photographs of different views of fibrin deposition of an in vitro fusiform model using whole blood after 30 minutes.

Figure 16:
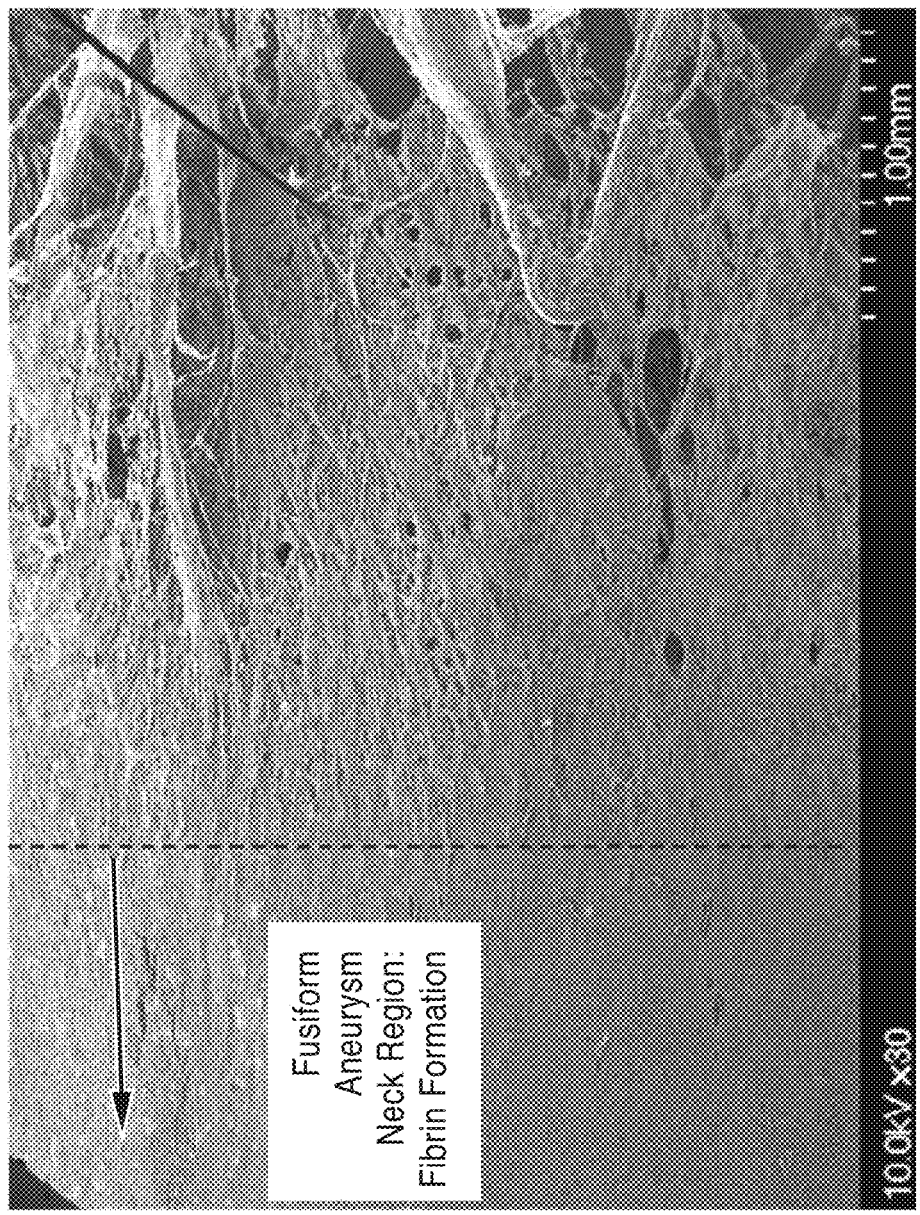

FIG. 16 shows an SEM image of fibrin deposition of in vitro fusiform model using whole blood after 30 minutes.

Figure 17:
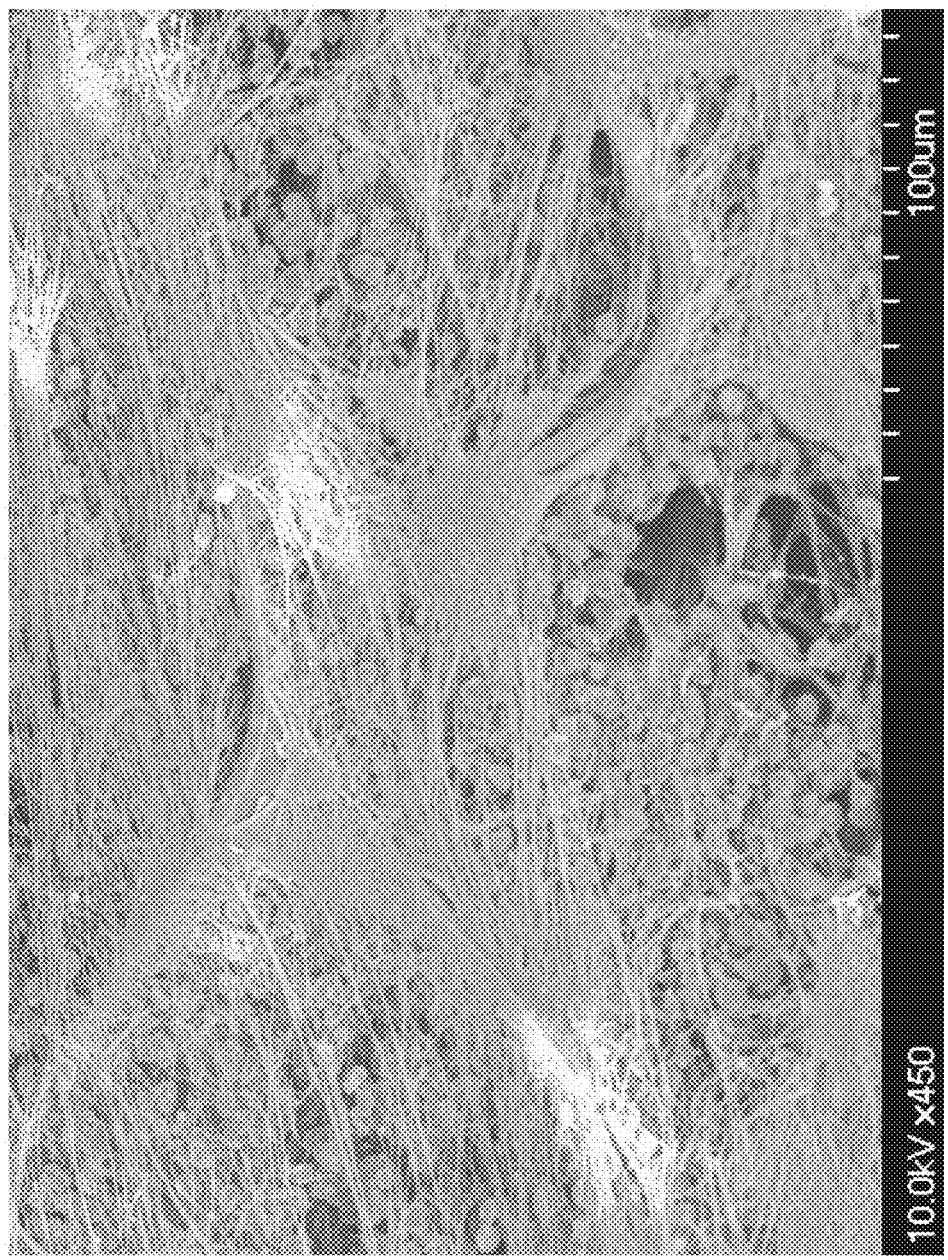

FIG. 17 shows a zoomed-in image of the left side of the SEM image of FIG. 16.

Figure 18A:

FIG. 18A image of angiogram showing a surgically place aneurism in the carotid artery of a swine.

Figure 18B:

FIG. 18B illustrates an angiogram of the same vessel of FIG. 18A immediately (<5 minutes) after deployment of the device of the present.

FIG. 19 is a photograph of the harvested aneurysm sac of FIGS. 18A and 18B approximately 2 hours after angiogram of FIG. 18B.

Figure 20:

FIG. 20 is an SEM image of the harvested aneurysm sac of FIG. 19, showing complete fibrin deposition of the implant.

Figure 21:
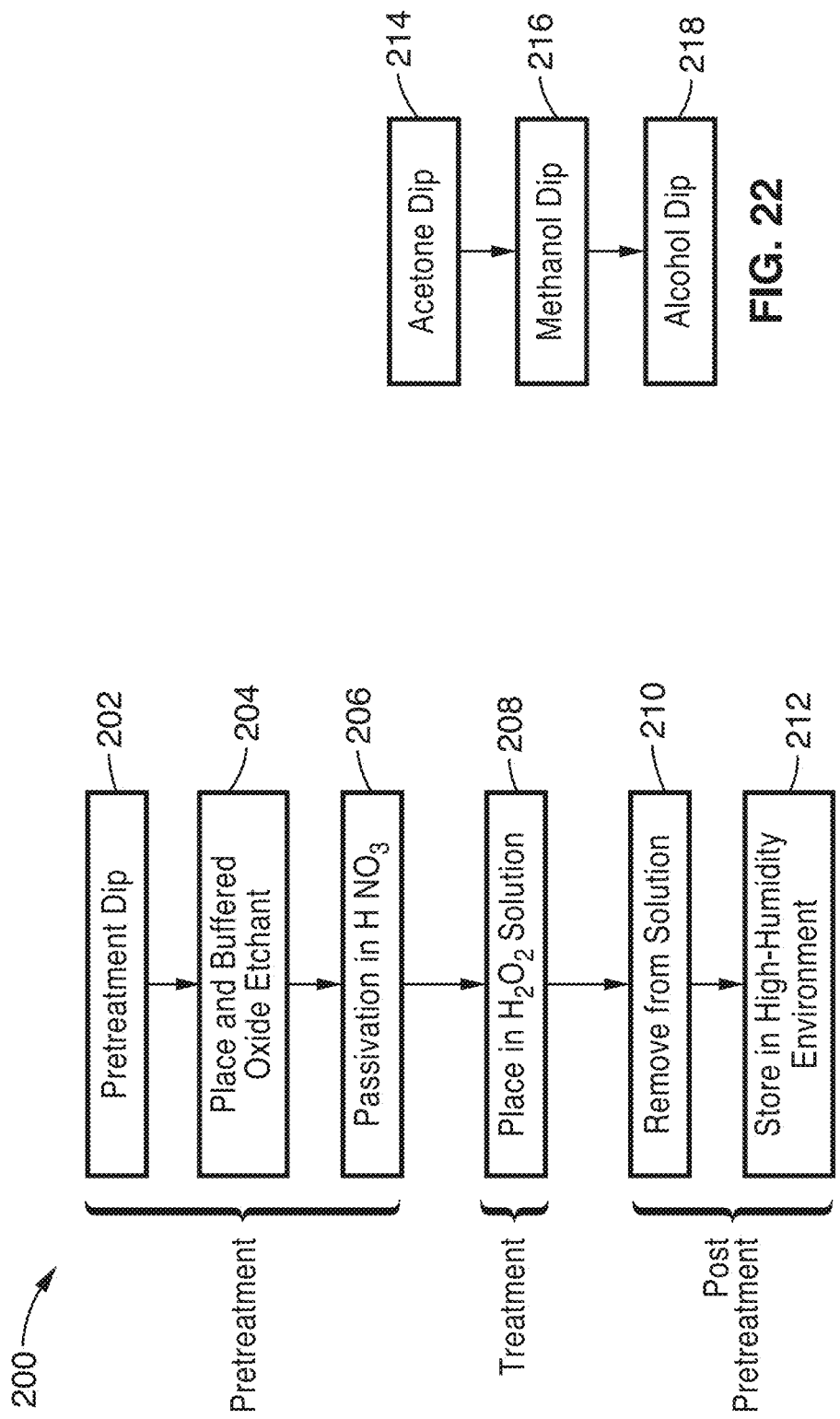

FIG. 21 illustrates an exemplary treatment method for generating a super hydrophilic thin film NiTi surface.

Figure 22:
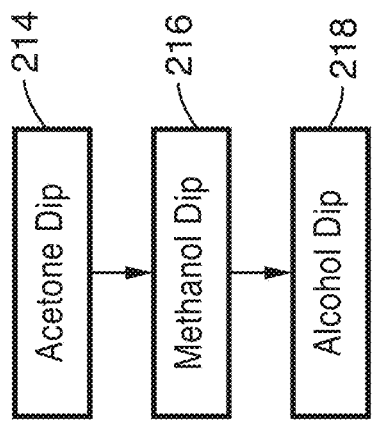

FIG. 22 is a flow diagram of a pretreatment dip used in the method of FIG. 21.

DETAILED DESCRIPTION OF THE INVENTION

FIG. 1 shows a schematic diagram of ultra-low profile micro-patterned thin-film flow diverter 10 placed in the small/broad-neck aneurysm site 12 of vessel 14. Vessel 14 generally has flow $F_A$ traveling in the direction from upstream end 16 of the aneurism site 12 to downstream end 18.

The flow diverter 10 generally comprises a micro-patterned thin-film Nitinol (representing a generic composition of NiTi) sheet 30 disposed over a collapsible stent 20 comprised of a plurality of connected members 22. In one embodiment, the thin-film sheet 30 may comprise diamond shaped holes on the order of 200 microns when deployed (300 microns as fabricated), and with and a percentage coverage area on the order of ~10% solid.

It may also be possible to deliver micro-patterned thin-film Nitinol sheet 30 (or other biocompatible material) to the neck of aneurysms with other devices, (i.e. devices other than commercially available stents). Because thin film structure 30 utilizes micro-fabrication processes coupled with thin-film metals to manufacture very small pore sizes (e.g. ~1-400 microns), it is not limited by the availability of either the wire mesh density or macroscopic structures that would not provide the flexibility, the physical dimensions, or the physical geometries required to both limit flow while also providing a sparse coverage.

While the present description focuses on a single layer of film 30 containing an array of perforations or holes, it is contemplated that the flow diverter 10 may also comprise a multiple layers film, each containing a wide range of holes.

Thin-film 30 may also configured to be "hyper-elastic," such that it elongates greater than 100% without permanent deformation. While this hyperelasticity is not is not necessary for flow diversion, it is advantageous for attaching film to a self-expanding device (e.g. stent 20) that can be collapsed into a small catheter and delivered in a transcatheter fashion.

The efficacy of the thin-film flow diverter 30 has been demonstrated both in vitro and in vivo, as will be shown in the description below. Thin-film flow diverter 30 is configured to be easily mounted onto a variety of scaffolds or structures, including stents (e.g. such as stent 20 shown in FIG. 1), and woven metallic structures, as well as other collapsible devices available in the art.

The particular example shown in FIG. 1 and throughout the foregoing disclosure comprises an ultra-low profile flow diversion device for neurovascular aneurysm treatment. However, it is contemplated that the flow diverter 10 may be configured as a device designed for flow diversion from a diversity of vascular imperfections, including thoracic and abdominal aortic aneurysms, pseudo-aneurysms, peripheral aneurysms, etc. Although most aneurysms are found in the brain, device 10 may function as a flow diverter for peripheral aneurysms such as those found in the splenic artery and renal arteries.

In addition to being used for aneurysm occlusion, the device of the present invention may be used to provide the flow diversion for occlusion of unwanted fistulas, including but not limited to ASDs (atrial septal defects), VSDs (ventricular septal defects allowing mixing of blood from left and right ventricles), occlusion of the LAA (left atrial appendage, to prevent blood clot formation in atrial fibrillation), and PDAs (patent ductus arteriosus, a fistula between the aorta and pulmonary artery). Generally, these unwanted cardiac communications have also been classically treated with transcatheter devices. Although these lesions are very high flow and often have high pressure gradients across them, these lesions may be treated by providing occlusion with a modified version of thin-film 30.

FIG. 2 illustrates a diagram of a heart 40 having an Atrial Septal Defect (ASD) 48 within the atrial wall 46. Defect 48 generally comprises a perforation in the heart wall 46 that allows problematic blood flow 50 from in between the right atrium 44 and left atrium 42 allowing mixing of blood from left and right atria.

FIG. 3 shows an exemplary flow diverter assembly 60 installed in a location within a patient's heart to treat an Atrial Septal Defect (ASD) 48. The device 60 generally comprises micropatterned thin-film Nitinol sheets 62 supported by support structures 64 and 66. Support structures 64 and 66 are configured to enclose left and right sides of the fistula 48 in atrial wall 46 via central member 68 that passes through the perforation 48. The thin-film sheets 62, while perforated, are configured (and/or potentially surface treated) to promote fibrin deposition within the lattice network of perforations to occlude flow between the fistula 48.

FIGS. 4A through 4H show images of thin-film flow diverters of the present invention having various sizes and shapes of patterns fabricated with the lift-off microfabrication process described in further detail below.

Figure 4A:
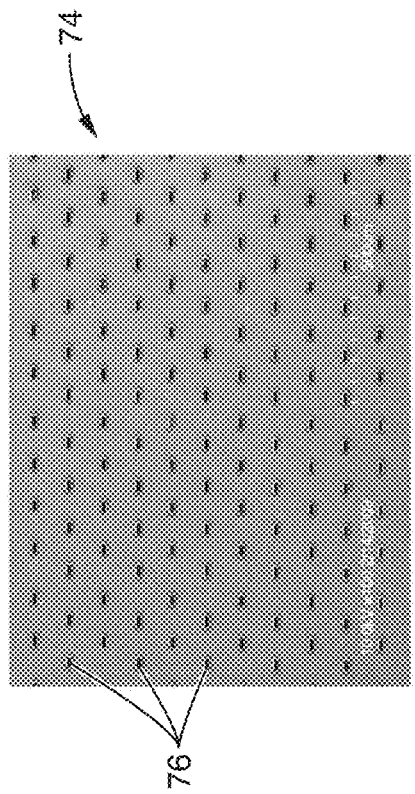
FIGS. 4A through 4H show images of thin-film flow diverters of the present invention having various sizes and shapes of patterns fabricated with a lift-off microfabrication process.
Figure 4B:
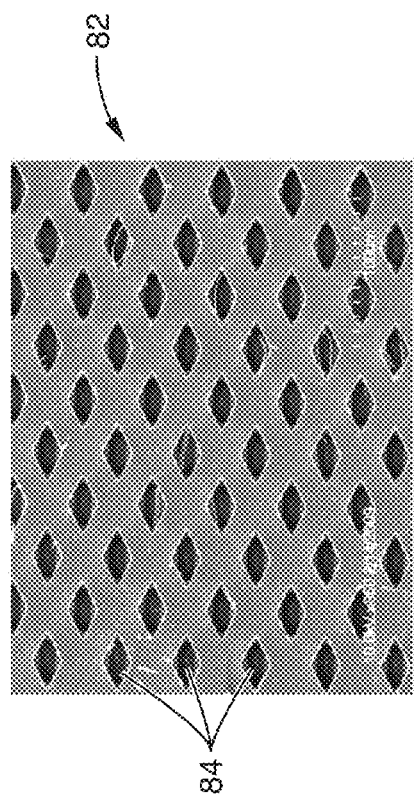
Figure 4C:
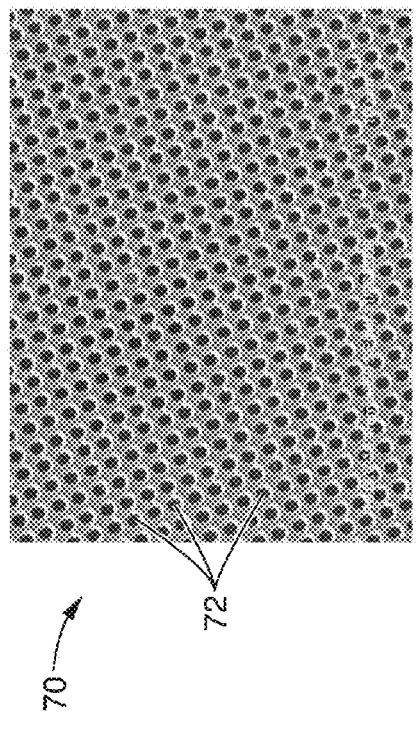
Figure 4D:
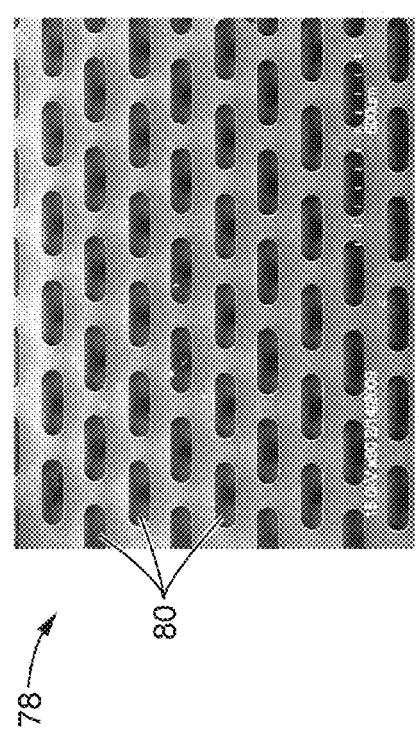
Figure 4E:
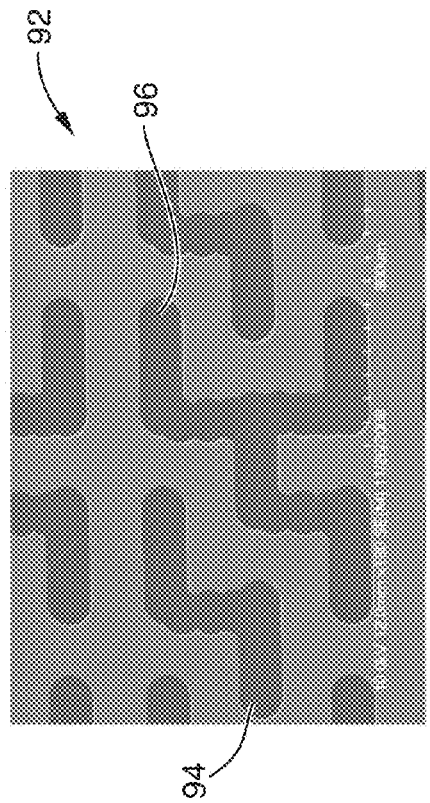
Figure 4F:
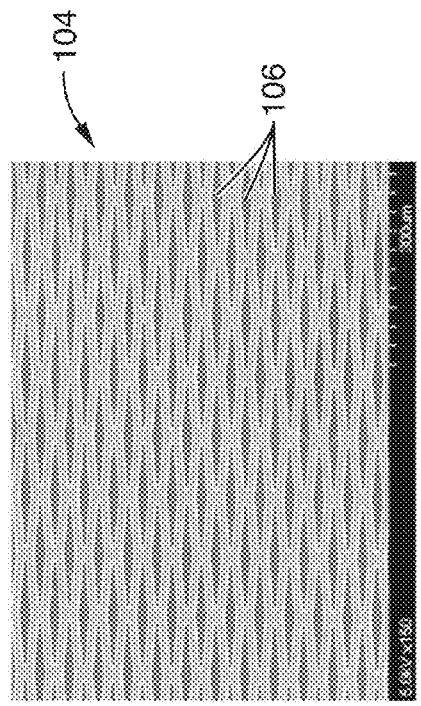
Figure 4G:
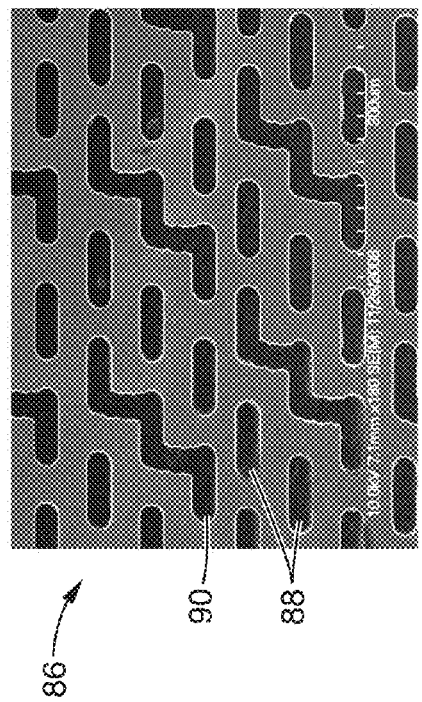
Figure 4H:
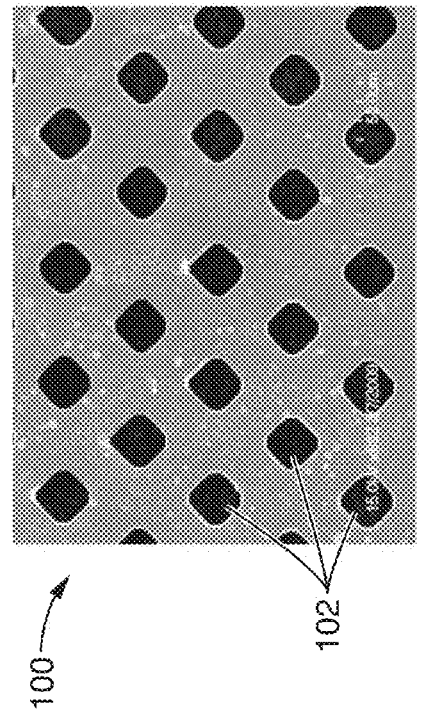

FIG. 4A shows a SEM image of a thin-film sheet 70 having a pattern of 5 micron circular fenestrations or holes 72. This thin film sheet can be from a wide range of Nitinol compositions (including ternary compositions) as well as from the general class of metals including Ti. FIG. 4B shows a SEM image of a thin-film sheet 74 having a pattern of 20×10 micron elliptical holes 76. FIG. 4C shows a SEM image of a thin-film sheet 78 having a pattern of 105×75 micron elliptical holes 80. FIG. 4D is a SEM image of a thin-film sheet 82 having a pattern of 40×30 micron diamond holes 84. FIG. 4E shows a SEM image of a thin-film sheet 86 having a pattern of 100×50 micron ellipse 88 and connected ellipse 90 fenestrations. FIG. 4F shows a SEM image of a thin-film sheet 92 having a pattern of 180×60 micron connected ellipse fenestrations 94 and 96. FIG. 4G is a SEM image of a thin-film sheet 100 having a pattern of 20×20 micron rectangular holes 102. FIG. 4H is a SEM image of a thin-film sheet 104 having a pattern of 150 micron diamond holes 106.

FIGS. 5A through 7B show images of hyper-elastic thin-film flow diverters of the present invention having various shaped patterns fabricated with the lift-off microfabrication process.

Figure 5A:
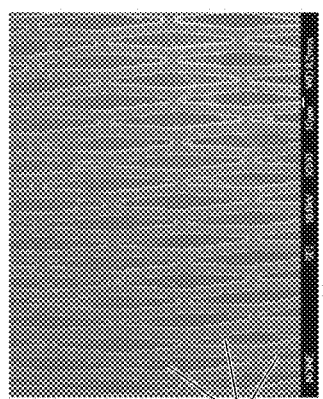
FIG. 5A shows an image of a 150 micron diamond-patterned thin-film flow diverter prior to elongation.
Figure 5B:
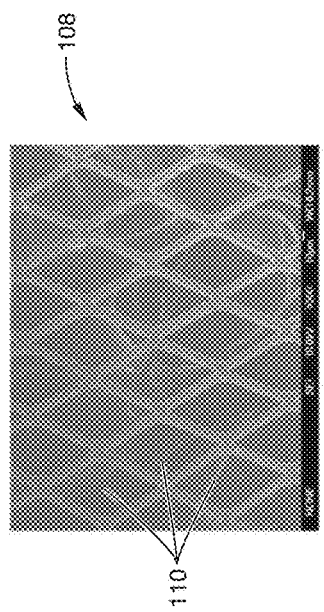
FIG. 5B shows an image of a 150 micron diamond-patterned thin-film flow diverter after elongation.

FIG. 5A shows an image of a thin-film flow diverter 108 with 150 micron diamond-shaped fenestrations 110 prior to elongation. FIG. 5B shows the 150 micron diamond-patterned thin-film flow diverter 108 of FIG. 5A after elongation.

Figure 6A:
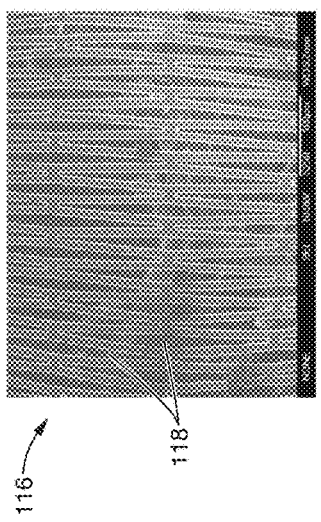
FIG. 6A shows an image of a 300 micron diamond-patterned thin-film flow diverter prior to elongation.
Figure 6B:
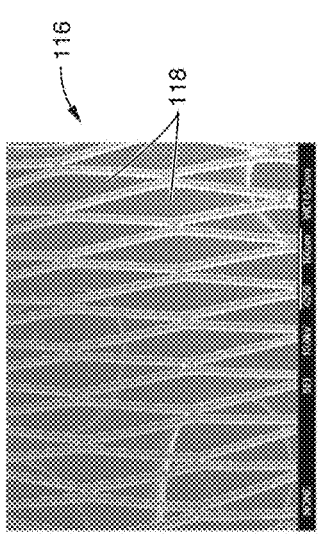
FIG. 6B shows an image of a 300 micron diamond-patterned thin-film flow diverter after elongation.

FIG. 6A shows an image of a thin-film flow diverter 116 with 300 micron diamond-shaped fenestrations 118 prior to elongation. FIG. 6B shows the 300 micron diamond-patterned thin-film flow diverter 116 of FIG. 6A after elongation.

Figure 7A:
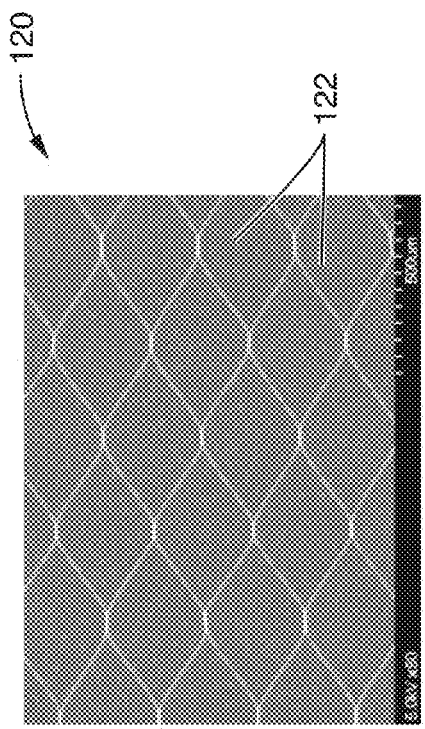
FIG. 7A shows an image of a 500 micron diamond-patterned thin-film flow diverter prior to elongation.
Figure 7B:
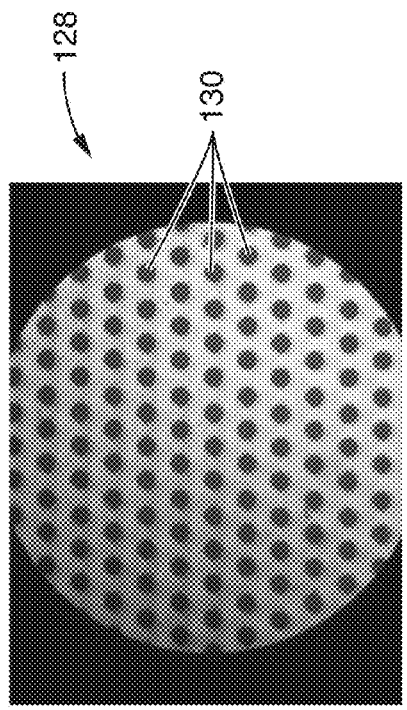
FIG. 7B shows an image of a 500 micron diamond-patterned thin-film flow diverter after elongation.

FIG. 7A shows an image of a thin-film flow diverter 120 with 500 micron diamond-shaped fenestrations 122 prior to elongation. FIG. 7B shows the 500 micron diamond-patterned thin-film flow diverter 120 of FIG. 7A after elongation.

Figure 8A:
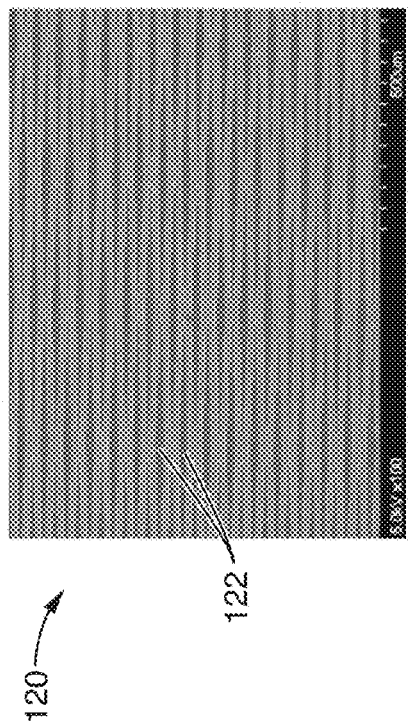
FIGS. 8A through 8D show images of thin-film flow diverters of the present invention having various sized circular or elliptical shaped patterns.
Figure 8B:
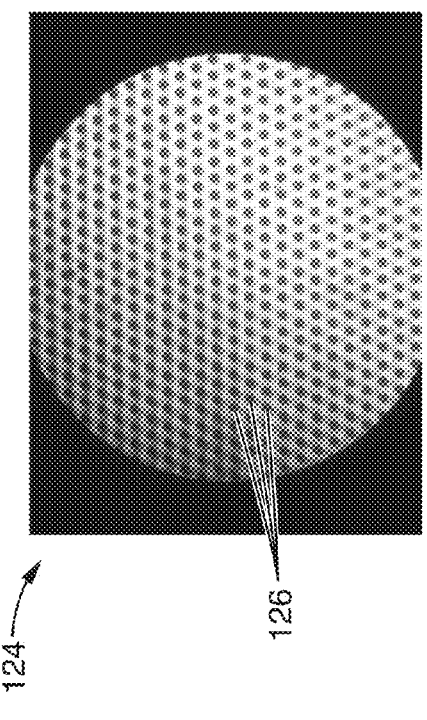
Figure 8C:
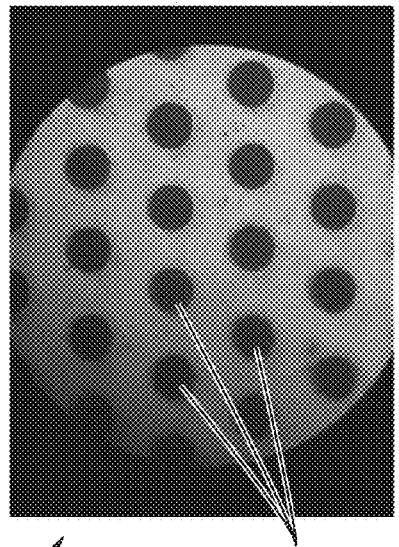
Figure 8D:
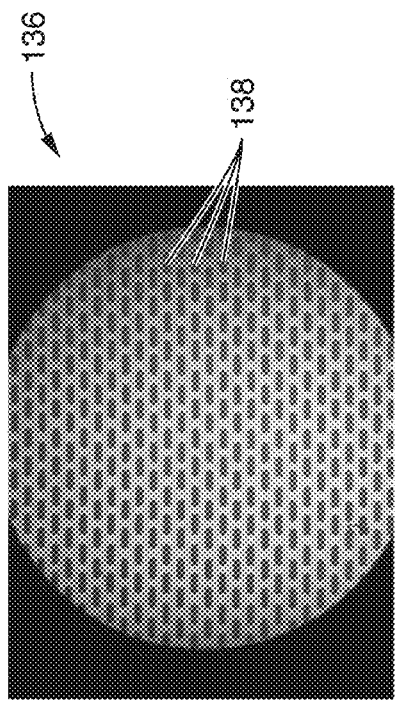

FIGS. 8A through 8D show images of thin-film flow diverters of the present invention having patterns fabricated with the lift-off microfabrication process that have rounded edges, such as circular and elliptical fenestrations. FIG. 8A shows an image of a thin-film flow diverter 124 with 20 micron circular fenestrations 126. FIG. 8B shows an image of a thin-film flow diverter 128 with 40 micron circular fenestrations 130. FIG. 8C shows an image of a thin-film flow diverter 132 with 80 micron circular fenestrations 134. FIG. 8D shows an image of a thin-film flow diverter 136 with 60×20 micron elliptical fenestrations 138.

FIGS. 10A through 11B show flow diverters comprising hyper-elastic, high-porous film disposed over separate stents. FIGS. 10A and 10B show two views of a flow diverter 160 comprising a hyper-elastic, high-porous thin film 160 disposed over a Neuroform stent 164. FIGS. 11A and 11B show two views of a flow diverter 170 comprising a hyper-elastic, high-porous thin-film 172 disposed over a pfm stent 174.

Contrary to conventional wisdom, the extremely small diameter fenestrations shown in the various thin films of the present invention depicted in FIGS. 4A through 8D are extremely effective flow diverters, despite their low surface coverage. Flow diversion tests are shown and discussed below for the thin films of FIGS. 5A, 5B, 6A, 6B, 7A and 7B. The change in size of the fenestrations from the fabricated state to the deployed state is illustrated in these figures. In addition, other flow diverter sizes and shapes have been fabricated as illustrated in FIGS. 4A through 8D.

The micro-machined Nitinol thin-film 30 of the present invention allows for the production of devices which only require 5-20% surface coverage, compared to existing devices that require greater than 30% coverage. Coverage area is defines as percent coverage of the structure (e.g. 100% coverage would be a solid material). Similar strategies could also be used with thin films created from a variety of other metals and organic and inorganic substrates. It is typically believed that surface coverage of greater than 30% is required to adequately quiesce a neurovascular aneurysm. Current teachings in the art suggest that flow diverters with less than 30% coverage are ineffective in many applications such as a brain aneurysm (see Satoshi Tateshima et al., *Alteration of intraaneurysmal hemodynamis by placement of a self-expandable stent*, J Neurosurg, 111:pp. 22-27, 2009.)

However, constructing such devices with less surface coverage allows for the production of less thrombogenic devices which are less likely to occlude the parent or perforating vessels. Combining low surface coverage with thin films also allows for the production of flow diversion devices with an unprecedented low profile. This is extremely important for certain vascular regions in the body such as intercranial applications.

The thin-film 30, having surface coverage less than 15%, creates rapid thrombosis within the aneurysm sac 12, thus preventing possible ruptures with minimal coverage of the vessel wall 14. Accordingly, device 10 reduces the chance that the parent vessel will be occluded by thrombus, and decreases the chances of occluding vital perforating arteries in close proximity to the aneurysm being treated. Furthermore, since substantially smaller amounts of material are used in the device 10, the size of the delivery system will also be reduced.

Fabrication of Micro Machined Thin-Film Nitinol Sheets and Flow Diverters

All the fabricated films shown in FIGS. 4A-8D contained holes or fenestrations which extended through the entire thickness of the film. Generally, the thickness of the thin films preferably ranges between about 2 µm and about 12 µm, and more preferably between about 6 µm and about 8 µm. For many transcatheter applications, it is also desirable to have the fabricated films to be extremely flexible. To achieve large strains, both phase transformation and structural issues were considered as well as the types of holes fabricated. Structural behaviors of specific hole shapes were first investigated to find design patterns that produced hyper-elastic strain with minimal buckling. Four different configurations were used that accommodate strains ranging between 100-800% without failure, and are shown in FIGS. 5A through 7B and 10A through 11B. This elongation itself represents a major advancement, since most currently produced metallic or Nitinol structures can only produce approximately 10% elongation or less.

While highly beneficial in certain applications, it is appreciated that the hyper-elastic component is not necessary for the flow diverter 10 of the present invention. The flow diverter 10 may be combined with other properties that are amenable specifically for all transcatheter applications. For example, in the treatment of brain aneurysms, it may be beneficial for the flow diverter 10 to have maximum elasticity so that it may be collapsed into a very small diameter catheter and subsequently deployed into a very large diameter vessel. Therefore, in this particular example hyperelasticity combined with a flow diverter is a desirable attribute.

The thin films shown in FIGS. 4A through 8B and 10A through 11B were fabricated by hot-target sputter deposition in combination with a lift-off micro machining method of the present invention. This lift-off method creates trenches on the Si substrate using photolithography and dry etching technique. The first step in the lift-off method for producing porous thin-film Nitinol is to create 50 µm deep trenches using conventional photolithography and deep reactive ion etching (DRIE) technique. Following this, 500 nm Cu sacrificial layer and 500 nm $SiO_2$ barrier layer deposited by e-beam evaporation and PECVD techniques, respectively. The thin-film Nitinol is deposited by DC sputtering process onto the $SiO_2$. Cu and $SiO_2$ layers are removed and stand alone film is crystallized at 500° C. for 120 minutes in a vacuum of less than $1\times10^{-7}$ torr. The fabricated porous thin-film Nitinol confirms the material superelastic properties at 36.5° C.

Figure 9:
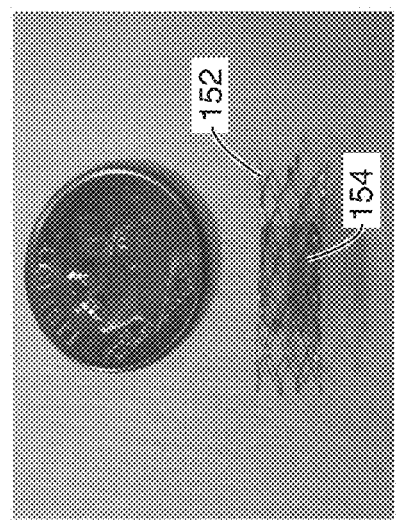
FIG. 9 shows an image of a stent assembly having an ultra-low profile fractional area coverage flow diverter using micropatterned thin-film Nitinol.

FIG. 9 shows an image of a stent assembly 150 having an ultra-low profile fractional area coverage flow diverter using micropatterned thin-film Nitinol sheet 152 over stent 154.

The 6 µm thick micropatterned Nitinol thin-film sheet 152 is covered over commercially available neurovascular and peripheral stent 154 and is adhered using either polymer adhesive, laser welding or suturing. Other micromechanical devices may also be used to adhere thin films to stents or other structures designed to deploy patterned thin films as flow diversion devices. Commercially available 3.5 mm and 4 mm neurovascular stents as well as 6 mm self-expanding stents intended for peripheral use were used with micropatterned thin films for laboratory and animal testing.

In order to minimize any possible thrombosis in the parent artery, super-hydrophilic surface treatments (such as that provided in PCT International Application No. PCT/US2010/026430 filed on Mar. 5, 2010, published on Sep. 10, 2010 as PCT International Publication No. WO 2010/

102254, and republished on Jan. 20, 2011) may preferably be performed prior to or following attachment of the film.

FIG. 21 illustrates an exemplary treatment method 200 for generating a super hydrophilic thin film NiTi surface in accordance with the present invention. A thin film NiTi sheet is generated using a DC sputter deposition technique as follows: A near equiatomic NiTi alloy target is placed under UHV (ultra-high vacuum) atmosphere. The base pressure of the sputter chamber is set below $5 \times 10^{-8}$ Torr and the Ar pressure was $1.5 \times 10^{-3}$ Torr. A 4" silicon wafer is used as a substrate with a 5000 Å thick silicon dioxide layer. To minimize compositional variations, the wafer is translated in 80 mm lengths perpendicular to the heated NiTi target. Films (i.e., 6 μm thick) are fabricated with a deposition rate of 0.1 μm/min. Following deposition, the film is mechanically removed from the wafer and crystallized at 500° C. for 120 minutes in a vacuum less than $10^{-7}$ Torr.

The thin film is first pretreated according to steps 202, 204, and 206. In one embodiment shown in FIG. 22, a cleaning pretreatment dip 202 comprises sequentially dipping the film in acetone at 214, methanol at 216, and finally alcohol at 218 for 5 minutes. At step 204, the film is subsequently placed in a buffered oxide etchant (BOE: aqueous $NH_4$—HF etchant) to eliminate the native oxide layer. Next, the film undergoes passivation in a nitric acid ($HNO_3$) solution (e.g. 30%) for 40 min at step 206. It is appreciated that while the above steps may be optimal for pretreating the film, one or more of the above pretreatment steps may be modified or omitted. For example, the total pretreatment process may simply comprise the passivation step 206.

At step 208, the thin film NiTi is then surface treated using a hydrogen peroxide treatment which comprises placing the film in a concentration of hydrogen peroxide ($H_2O_2$) solution mixed with deionized water at a specified temperature for a specified period of time. It is appreciated that the ideal treatment (e.g. for creating a super hydrophilic surface) is a function of the concentration of $H_2O_2$, time, and temperature (e.g. $HPT_{d,f,g}$, where d=$H_2O_2$ concentration, e.g. 3-30%, f=temperature, e.g. 25° C. or 110° C., and g=time, e.g. 0.5~15 hrs). For example, a super hydrophilic surface may be achieved by immersion of thin film NiTi in a $H_2O_2$ concentration of 30% at 25° C. for 15 hours. It is appreciated that in an increased temperature, e.g. boiling at 110° C., and/or concentration percentage, may result in a super hydrophilic surface being achieved in less time.

At step 210, the film is then removed from the $H_2O_2$ solution, and then stored in a high humidity environment at step 212. Step 212 is configured to maintain the surface condition of the super hydrophilic surface generated from the treatment step 208 without decaying of hydrophilicity. In one embodiment, step 212 comprises fully immersing the film in a deionized water (DI) solution. Alternatively, the film may be contained in high humidity air (e.g. >90% humidity) via a humidifying element, humidor, or the like.

Storage of the film in a high humidity environment, as detailed above in treatment method 200, aids in preventing the release of the hydroxyl groups. While reducing the wetting angle, the hydroxyl groups bound to the surface are unstable and are easily be decomposed in ambient air environment. By storing the surface treated thin film in a high humidity environment (e.g. step 212), decay of super hydrophilicity is prevented. In one embodiment, step 212 comprises placing a fully saturated deionized (DI) water cloth in a vacuum bagged container along with the treated thin film. The thin film may be coiled inside a catheter for ready installation for a desired procedure. While the above preservation approach may be the most practical, it is contemplated that other preservation/hydration processes may also be employed.

Generally, the super-hydrophilic surface will a water contact angle of less than approximately 5 degrees, and/or be configured to deter platelet adhesion at a rate of less than 3 parts per $mm^2$ when subjected to platelet rich plasma for 3 or more hours. As detailed below, experimental results found thin film Nitinol sheets having this surface treatment act as a beneficial source for fibrin deposition to promote rapid occlusion of the desired region, in this example an aneurysm sac. Such results are unexpected, as conventional understanding would generally lead one skilled in the art to expect that a surface highly effective in deterring platelet adhesion would also deter fibrin deposition. However, the process above for generating a super-hydrophylic surface results in a significantly increased oxide layer (TiO) having negatively charged hydroxyl groups. It is believed that these negatively charged ions attract the positively charged fibrin, thus resulting in rapid fibrin deposition and occlusion.

Currently, the flow diverter manufactured with micropatterned thin-film Nitinol can be collapsed into 3Fr catheter when mounted onto neurovascular Neuroform stents from Boston Scientific. It is anticipated that this device will be able to be collapsed into and delivered by catheters even less than 3 Fr.

Based on the above models, small scale features can be produced in thin films Nitinol or of other metals. As detailed above, photolithography is used to produce physical features as small as a couple of microns. It should be noted that e-beam lithography may also be used to produce features as small as 5 nanometers. Therefore, the thin films of the present invention are not limited to feature sizes above 1 micron (see film 100 in FIG. 4G for 20 micron size patterns and film 70 in FIG. 4A for 5 micron sizes produced). When the porosity of physical feature decreases (e.g. smaller diameter holes), the line area around the feature divided by the total area increases. Therefore, as the feature size decreases this ratio increases. This is of vital importance because at the perimeter of the physical feature (e.g. circumference of the hole) there is a zero flow condition. Thus, as the ratio increases, even though the total porosity remains a constant, the net flow through the flow diverter will dramatically decrease.

By appropriately configuring the structure (e.g. this cannot currently be done with woven systems) the flow pattern can be further decreased. This can be achieved by introducing sharp corners as one example where flow stagnation is known to occur, as well as fabricating a specific shape relative to the flow velocity to produce stagnation. By making the physical dimensions of the pores on the order of blood products (e.g. red blood cells are 5-10 microns), the flow diverter 10 actually prevents flow and begins to act as a sieve that becomes clogged to prevent flow. Note, the latter can actually be achieved with nearly 0% coverage area. Even though the size of the holes is larger than blood products (e.g. holes on the order of 200 microns) they promote the almost immediate formation of fibrin depending upon the flow conditions, which can lead to an almost immediate cessation of flow. Thus, the above three physical features, coupled with one biological interaction, contribute to flow diversion in small scale structures that can be produced in a thin-film metal.

The thin-film Nitinol flow diversion device 10 of the present invention may be used for treatment of any small vessel aneurysm (aneurysms in vessels <6 mm) as well as many other flow diverters in the vascular system. The thin films of the present invention are compatible with even the most remote and wide-necked neurovascular aneurysms, as well as a wide range of other applications in larger vessels and even for intracardiac structures. Thus, the device is specifically amenable to the treatment of brain aneurysms:

(a) Delivery by transcatheter fashion in a delivery sheath less than or equal to 3 Fr (4 Fr delivery sheaths would be acceptable for larger 5 and 6 mm vessels harboring more proximal aneurysms);

(b) Delivery performed using standard neurovascular techniques, equipment and standards that have already been developed for delivery of commercially available stents to the necks of aneurysms'

(c) Sufficient flexibility to reach even small cranial vessels distal to the Circle of Willis;

(d) Ability to cause acute thrombus of aneurysms without significant effects on the parent vessel or on perforators. Preferably the porosity physical dimensions will be less than or equal to 400 microns and the percent coverage will be less than 20%.

Experimental Results

Referring now to FIGS. 12A through 14C, the efficacy of a flow diverter in accordance with the present invention having small pore size and small fractional coverage, was experimentally demonstrated.

Figure 12A:
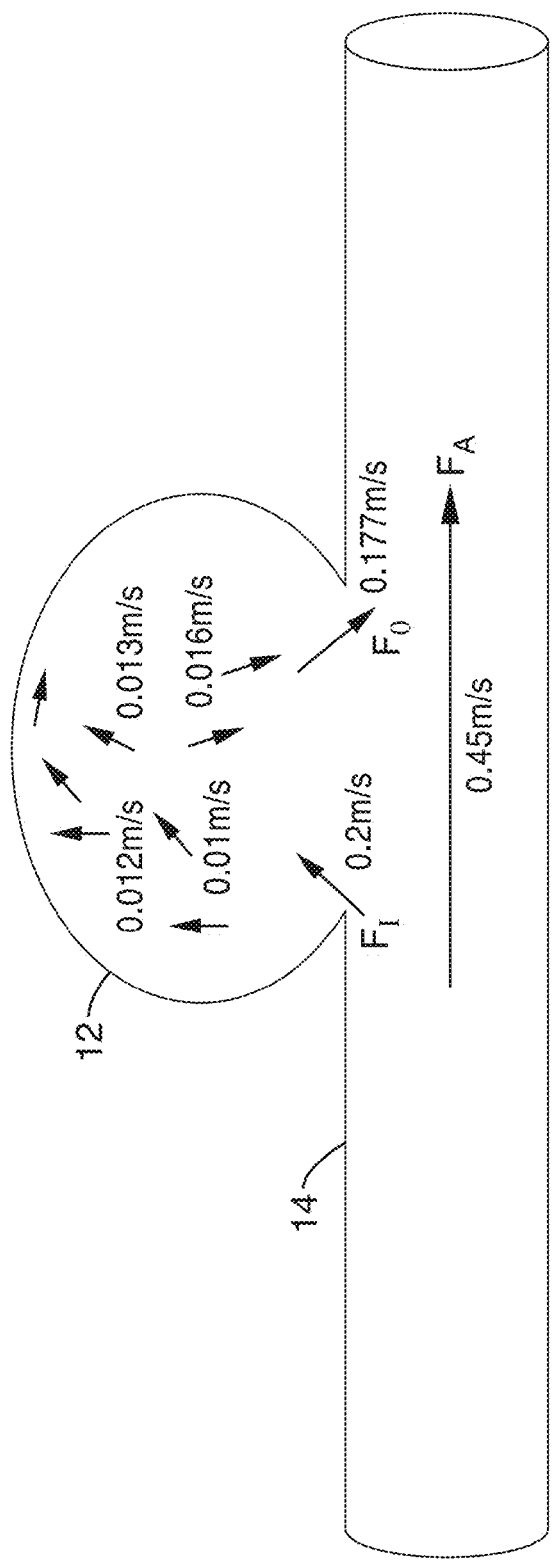
FIG. 12A illustrates a flow velocity profile of an aneurism without any flow diversion.
Figure 12B:
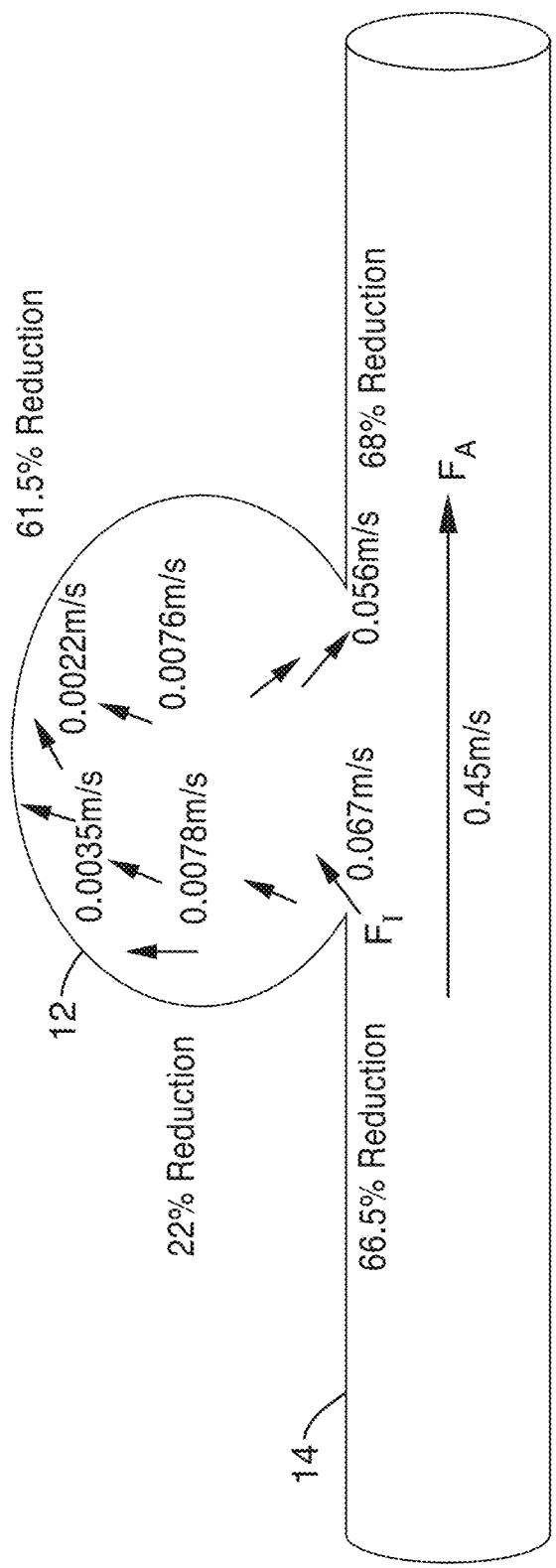
FIG. 12B illustrates a flow velocity profile of an aneurism without a present-art flow diverter installed.

FIG. 12A illustrates a flow velocity profile of an aneurism 12 without any flow diversion. The flow $F_A$ in the artery 14 is generally subject to diverted flow $F_I$ in and $F_O$ out of the aneurism 12. FIG. 12B illustrates the flow velocity profile of an aneurysm 12 without a presently available flow diverter installed. As shown in FIG. 12B, the flow in $F_I$ is reduced by 66.5% and flow out $F_O$ is reduced by 68%.

Figure 12C:
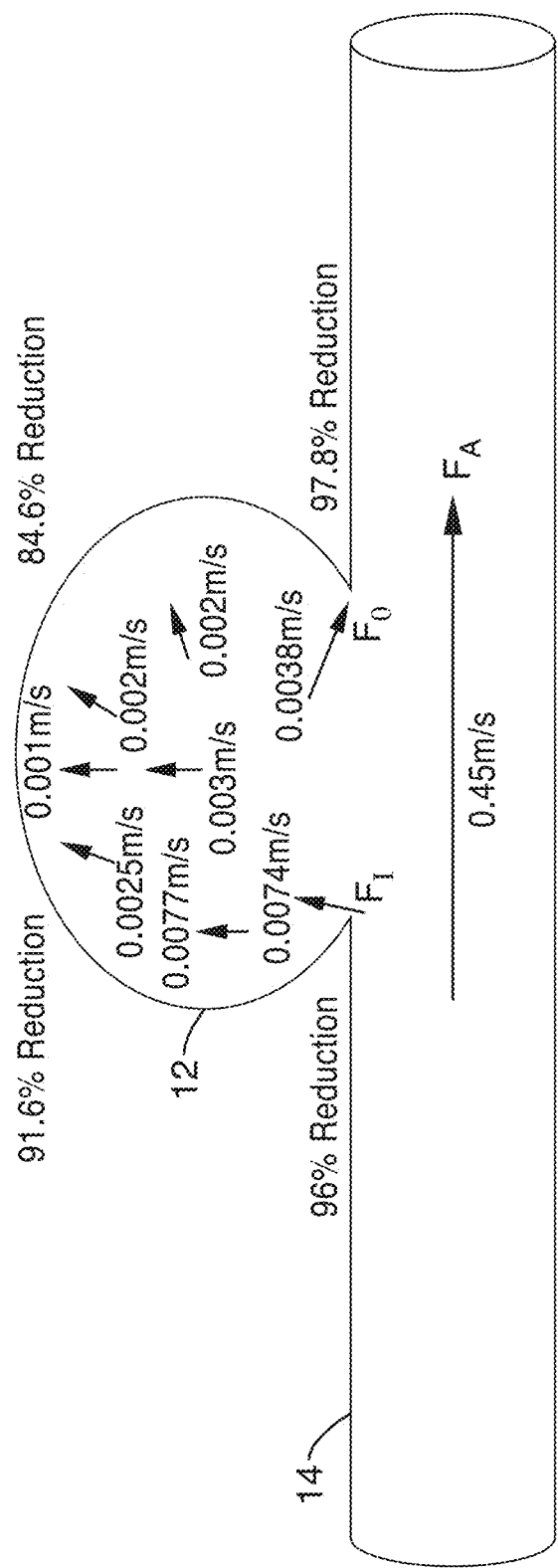
FIG. 12C illustrates a flow velocity profile of an aneurism with an ultra-low profile micropatterned thin-film Nitinol flow diverter of the present invention installed.

FIG. 12C illustrates a flow velocity profile of an aneurysm with an ultra-low profile micropatterned thin-film Nitinol flow diverter of the present invention installed. As shown in FIG. 12C, the flow in $F_I$ is reduced by 96% and flow out $F_O$ is reduced by 97.8%.

FIGS. 14A through 14C show a test to evaluate a flow diverter 10 in reducing flow in a simulated wide neck 12B or fusiform 12C aneurysm sac created from a plastic and/or glass mold 14. The size of the neck for both of these aneurysms was 8 mm and the diameter of the simulated vessel 14 was 4 mm. The flow conditions were stenotic. In these studies both 300 micron size (FIGS. 6A,B) and 500 micron size (FIGS. 7A,B) thin films were used on the device to evaluate the reduction of flow velocity into the aneurysm sac. It should be noted that when the flow diverter 10 is deployed into the simulated vessel 14, the representative total coverage area of the neck (12A-C) is less than 15%, as can be seen in the magnified images of diverter 160 shown in FIGS. 10A and 10B. In these tests, flow reductions on the order of greater than 90% compared to the sac without a flow diverter were achieved.

The largest flow reduction was achieved with the 300 micron size fenestrations 118 of the thin film 116 shown in FIGS. 6A and 6B. It should also be noted that in all of these tests the film had been treated with the super-hydrophilic surface treatment described above. The sparse coverage (as little as 10% or less) with small pore size (200 micron size pores of the fenestrated 5 micron thick thin-film 116) were found to significantly reduce (>90%) the intra-aneurismal flow velocity and vorticity.

FIG. 13A shows the percent reduction in flow velocity in wide neck aneurism sac 12b with 500 micron (FIGS. 7A,B) and 300 micron (FIGS. 6A,B) thin films installed. FIG. 13B shows the percent reduction in flow velocity in fusiform aneurism 12c with 500 micron (FIGS. 7A,B) and 300 micron (FIGS. 6A,B) thin films installed.

FIGS. 14A through 14C show flow diverters 10 of the present invention installed within different aneurism types: small neck aneurism 12a shown in FIG. 14A, wide neck aneurism 12b shown in FIG. 14B, and fusiform aneurism 12c shown in FIG. 14C) of in vitro models with human whole blood.

Referring now to FIGS. 15A through 20, in addition to the above in vitro studies with simulated blood, lab studies with whole blood also demonstrated a much quicker occlusion of a pseudo-aneurysm compared to a bare stent. Tests were performed on the device 150 shown in FIG. 9 (having thin-film sheet detailed in SEM images of FIGS. 6A, 6B and 10A-11B) in vivo, and showed the cessation of flow into an aneurysm sac almost immediately upon deployment (i.e. less than 5 minutes from first angiogram shot).

In vivo tests were conducted on swine with a surgically created aneurysm in the carotids. Both the left and right carotid had a surgically created wide neck aneurysm (approximately 7 mm neck in diameter). These aneurysms were occluded by deployment of the both the 200 (300) micron (thin film 116 in FIGS. 6A and 6B) and 400 (500) micron (thin film 120 in FIGS. 7A and 7B) size thin-film NiTi flow diverters across the neck of the aneurysms. Prior to deploying the thin-film flow diversion device onto the aneurysm sac, the aneurysm was widely patent, and free from any obstructions or clots as demonstrated by angiography (illustrated in the image of 18A). The first swine study used only 200 (300) micron size fenestrations of thin film 116 in FIGS. 6A and 6B with super-hydrophilic surface treatment.

FIG. 18B illustrates an angiogram of the same vessel in the image of FIG. 18A two minutes after deployment of the device of the present invention using the 300 micron fenestrated film 116 in FIGS. 6A and 6B. Total occlusion of aneurysm sac is achieved immediately following deployment of the device (i.e. first angiogram shot somewhere close to 2 minutes). Flow into the aneurysm sac was completely undetectable by the angiography shown by FIG. 18B. This test shows that the aneurysm had become hemodynamically quiescent or occluded within 0-2 minutes of flow diverter deployment. This phenomenon occurred in all aneurysms tested using the 200 (300) micron fenestrated film 116 in FIGS. 6A and 6B.

When this particular in vivo test was repeated on a separate swine study using 400 (500) micron diameter holes of thin film 120 in FIGS. 7A and 7B, it took approximately 30 minutes to 1 hour for flow to cease into the aneurysm sac. This result suggests an ideal or critical sized fenestration dependent upon anatomical features, such as flow velocity and vessel size, such that a designated fenestration size (with surface treatment) immediately occludes the sac due to the fast deposition of fibrin and other blood products onto the thin-film scaffolding. More importantly, even though the holes may not have been sized at the ideal or critical dimension, flow into these aneurysms was decreased sufficiently enough to produce quiescence of the aneurysm sac.

The flow diverter devices were harvested the same day they were deployed. Using both optical microscopy and SEM evaluation clear deposition of blood products on all the fenestrations was noted, most notably a fibrin structure mesh formed that prevented flow through the holes. FIGS. 15A and 15B show microscopic image photographs of different views of fibrin deposition of the in vitro fusiform 300 micron thin film 116 using whole blood after 30 minutes. FIG. 16 shows an SEM image of fibrin deposition of the same in vitro fusiform model using whole blood after 30 minutes. As shown in FIG. 16, the left of the dotted line is deposition created from thin film 116. FIG. 17 shows a zoomed-in image of the left side of the SEM image of FIG. 16.

FIG. 19 is a photograph of the harvested aneurysm sac of FIGS. 18A and 18B approximately 2 hours after angiogram of FIG. 18B, showing total occlusion of aneurism, and completely contained thrombii. FIG. 20 is an SEM image of the harvested aneurysm sac of FIG. 19, showing complete fibrin deposition of the implant.

When evaluating the results of these studies, it is readily apparent that after only a few minutes in the circulation system, fibrin begins to deposit onto the thin film fenestrations of the present invention flow diverters. The combination of the thin-film meshwork and fibrin begin impeding flow very quickly. Therefore, the flow reduction in a biological entity is likely attributed to both the fenestration limiting flow (e.g. as seen in the simulated blood experiments) but also from the rapid deposition of blood products such as fibrin on the thin film. The in vivo results described above demonstrate dramatic occlusion of even large aneurysm sacs.

This rapid fibrin deposition, or clotting cascade, is believed to be initiated by the unique structural configuration of the thin-film flow diverters of the present invention, i.e. the relative size of the fenestrations in the thin-film that begin to approach the physical dimensions of the blood products. To another extent, the surface treatment may also provide added fibrin deposition or clotting cascade functionality. The flow environment surrounding the thin-film is also a factor that influences the rate at which the device binds to blood products (especially fibrin).

The thin-film flow diverter of the present invention produces a dramatic effect on the flow dynamics into anatomical feature such as, for example, an aneurysm. This in turn activates the clotting cascade only within the aneurysm. The thin-film meshwork has also been shown both in vivo and in vitro to isolate the parent artery from the large thrombus within the aneurysm. Thus, the methods and devices of the present invention can not only cause rapid thrombus formation within an aneurysm, but also protect the native artery from embolization of this thrombus.

It is important to note that this clotting cascade does not occur rapidly in large diameter holes such as stents. Coverings on the order of 1 mm were tested, and did not result in fast deposition of fibrin that was observed in the small-dimension fenestrations of the thin films of the present invention. It is also noteworthy that the devices of the present invention do not produce thrombus formation within the parent artery. Long term in vivo studies have shown these devices to be free of clot and excessive neointimal hyperplasia in the parent arteries.

In conclusion, these studies found that ultra-thin high porous material can dramatically reduce the flow within the sac and could be used for any flow diverting vascular devices. This flow reduction is due in part to the geometry chosen, the decrease in pore size, and the increase in the relative surface area around the perimeter of the hole to surface area ratio (i.e. this value increases as hole size decreases even though surface coverage is constant). This flow diversion may also be partially attributed to the surface treatment that the film underwent prior to testing. Because thin-film Nitinol flow diverters of the present invention also allow for the creation of extremely flexible and low profile neurovascular flow diversion devices, this work represents a major breakthrough for this field that would have not been previously considered possible by the community. The -film Nitinol flow diverters of the present invention enable the creation of many different forms of flow diversion devices that are non-thrombogenic (reduction in surface area contacting blood), low profile, flexible and that can divert flow without negatively impacting the specific treatment proposed (e.g. for aneurysm flow diverter not occluding parent or perforating vessels).

Thin-film flow diverters of the present invention allow for the production of ultra-low profile neurovascular devices. Although Nitinol was used as the preferable material in these studies, it is contemplated that other materials may also be used for these applications. Not only are these devices lower profile than the current state of the art flow diversion device (Pipeline Stent, EV3), but they are much more flexible, less thrombogenic, and have significantly lower percent coverage of the aneurysm sac (i.e. compare 10-20% to 30% for Pipeline). The present invention flow diverters allow for use of the most minimal amounts of material necessary for the treatment of small aneurysms. The flow diverter of the present invention may be collapsed in a 3Fr microdelivery catheter, delivered through highly tortuous vascular structure, and deployed with self-expanding mechanism to create intra-aneurismal thrombosis in short time periods with minimal occlusion of perforating vessels.

The device of the present invention also provides a particular advantage in preventing thrombus from migrating from the sac of a broad neck or fusiform aneurysm into the parent vessel (e.g. prevents strokes). The device of the present invention provides particular unexpected thrombotic effects with respect to the aneurysm that have protective effects to the parent vessel. Specifically, once the device of the present invention is covered in native proteins, it is even more invisible to the parent vessel, and less likely to induce clots in the parent vessel.

While the above advantages are directed to one particular application, it is appreciated that the flow diverter of the present invention can be used in a wide range of other vascular applications.

In summary, the above description details a diversion device that has minimal surface area, but produces dramatic changes in flow patterns. Specifically for the brain aneurysm problem, researchers have long believed based on available literature that coverage areas must be greater than 30% to achieve occlusion. The findings of the present invention have has shown that this is not the case for appropriately fenestrated thin films. Thus, the results of the present invention are unexpected in light of the previous literature, which has taught away from using less that 30% coverage to achieve occlusion.

It will be appreciated, therefore, that the invention can be embodied in various ways, which include but are not limited to the following.

1. A flow diversion apparatus for diverting blood flow from a treatment region, comprising: a thin-film sheet configured to be positioned adjacent the treatment region; the thin-film sheet comprising a plurality of fenestrations; wherein the fenestrations are sized to generate a clotting cascade at the treatment region.

2. A flow diversion apparatus according to embodiment 1: wherein the treatment region comprises an aneurism; and wherein the clotting cascade is configured to occlude the aneurism.

3. The flow diversion apparatus of embodiment 1, wherein the fenestrations have a pore size of less than approximately 500 microns.

4. The flow diversion apparatus of embodiment 3, wherein the fenestrations have a pore size of less than approximately 300 microns.

5. The flow diversion apparatus of embodiment 3, wherein the fenestrations have a pore size between approximately 200 microns and 400 microns.

6. The flow diversion apparatus of embodiment 1, wherein the thin-film sheet comprises a surface coverage of less than approximately 30%.

7. The flow diversion apparatus of embodiment 6, wherein the thin-film sheet comprises a surface coverage of between approximately 5% and 20%.

8. The flow diversion apparatus of embodiment 1, wherein the thin-film sheet comprises thin-film Nitinol having at least one super-hydrophilic surface.

9. The flow diversion apparatus of embodiment 8, wherein the super-hydrophilic surface has a water contact angle of less than approximately 5 degrees.

10. The flow diversion apparatus of embodiment 8, wherein the super-hydrophilic surface is configured to deter platelet adhesion at a rate of less than 3 parts per $mm^2$ when subjected to platelet rich plasma for 3 or more hours.

11. The flow diversion apparatus of embodiment 1, wherein the fenestrations comprise at least one sharp edge.

12. The flow diversion apparatus of embodiment 11, wherein the fenestrations comprise diamond-shaped apertures.

13. The flow diversion apparatus of embodiment 3, wherein the fenestrations are fabricated using micro-machined thin-film Nitinol.

14. The flow diversion apparatus of embodiment 1, wherein the fenestrations are fabricated using steps comprising: creating trenches using photolithography and deep reactive ion etching (DRIE); and depositing a Cu sacrificial layer and 500 nm SiO2 barrier layer by e-beam evaporation and PECVD.

15. The flow diversion apparatus of embodiment 1, wherein the fenestrations are configured to promote rapid binding of fibrin to the thin-film sheet.

16. The flow diversion apparatus of embodiment 1, further comprising: a collapsible stent; wherein the thin-film sheet is disposed over the stent.

17. A vascular implant for occluding an aneurism, comprising: a thin-film sheet configured to be positioned adjacent the treatment region; the thin-film sheet comprising a plurality of fenestrations; wherein the fenestrations are sized to generate a clotting cascade at the aneurism.

18. The vascular implant of embodiment 17, wherein the fenestrations have a pore size between approximately 200 microns and 400 microns.

19. The vascular implant of embodiment 18, wherein the thin-film sheet comprises a surface coverage of between approximately 5% and 20%.

20. A method of fabricating a thin-film sheet comprising an array of fenestrations, the fenestrations having a pore size of less than approximately 500 microns with a shape and size that is substantially identical throughout the array, the method comprising: creating trenches in a thin-film sheet of material using photolithography and deep reactive ion etching (DRIE); and depositing a Cu sacrificial layer and 500 nm $SiO_2$ barrier layer by e-beam evaporation and PECVD.

21. The method of embodiment 20, wherein the thin film comprises Nitinol, the method further comprising: depositing Nitinol by DC sputtering process onto the SiO2; removing the Cu and SiO2 layers; and crystallizing remaining film at 500° C. for 120 minutes in a vacuum of less than $1\times10^{-7}$ torr.

22 The method of embodiment 20, wherein the fenestrations have a pore size between approximately 200 microns and 400 microns.

23. The method of embodiment 20, wherein the thin-film sheet comprises a surface coverage of less than approximately 30%.

24. The method of embodiment 20, wherein the thin-film sheet comprises a surface coverage of between approximately 5% and 20%.

25. The method of embodiment 20, wherein the fenestrations comprise at least one sharp edge.

26. The method of embodiment 25, wherein the fenestrations comprise diamond-shaped apertures.

27. The method of embodiment 25, wherein the thickness of the thin-film sheet ranges between about 4 μm and about 12 μm.

28. The method of embodiment 25, wherein the thickness of the thin-film sheet ranges between about 6 μm and about 8 μm.

29. The method of embodiment 25, wherein the thin-film sheet is configured to elongate to over 400% of is original size without substantial deformation.

30. A method for diverting blood flow from a treatment region, comprising: delivering a flow diverter to the treatment region; and generating a clotting cascade at the treatment region.

31. The method of embodiment 30, wherein the flow diverter comprises a thin-film sheet having an array of fenestrations have a pore size between approximately 200 microns and 400 microns.

32. The method of embodiment 31, wherein the thin-film sheet comprises a surface coverage of less than approximately 30%.

33. The method of embodiment 32, wherein the thin-film sheet comprises a surface coverage of between approximately 5% and 20%.

34. The method of embodiment 31, wherein the thickness of the thin-film sheet ranges between about 6 μm and about 8 μm.

35. The method of embodiment 31, wherein the fenestrations are configured to promote rapid binding of fibrin to the thin-film sheet.

36. A method for occluding blood flow at an aneurism of a vessel, comprising: delivering a vascular implant to the aneurism; and generating a clotting cascade at the aneurism.

37. The method of embodiment 36, wherein the vascular implant comprises a thin-film sheet having an array of fenestrations have a pore size between approximately 200 microns and 400 microns.

38. The method of embodiment 30, further comprising preventing thrombus from migrating from the aneurism to the vessel.

39. The method of embodiment 38, wherein the aneurism comprises a broad neck or fusiform aneurism.

40. The method of embodiment 37, wherein the thin-film sheet comprises a surface coverage of between approximately 5% and 20%.

41. The method of embodiment 37, wherein the thickness of the thin-film sheet ranges between about 6 μm and about 8 μm.

42. The method of embodiment 37: wherein the fenestrations are configured to promote rapid binding of fibrin to the thin-film sheet; and wherein said rapid binding of fibrin results in substantial occlusion of flow into the aneurism within one hour of delivering the flow diverter to the treatment region.

Although the description above contains many details, these should not be construed as limiting the scope of the invention but as merely providing illustrations of some of the presently preferred embodiments of this invention.

Therefore, the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A flow diversion apparatus for diverting blood flow from a treatment region, comprising:
    a thin-film stent cover configured to be positioned adjacent the treatment region, the thin-film stent cover comprising a plurality of fenestrations and fabricated with a lift-off process comprising the steps of:
        creating a plurality of trenches using photolithography and deep reactive ion etching (DRIE) on a substrate;
        depositing a metal sacrificial layer on the substrate;
        depositing Nitinol on the metal sacrificial layer by sputtering to form a thin-film Nitinol comprising the fenestrations;
        removing the metal sacrificial layer;
        crystallizing the thin-film Nitinol to form the thin-film stent cover; and
        elongating the thin-film stent cover;
    wherein the fenestrations are diamond-shaped subsequent to the elongating of the thin-film stent cover;
    wherein the thin-film stent cover is hyper-elastic, such that it is capable of elongating to at least 400% without failure; and
    wherein the thin-film stent cover has a surface coverage of less than 20% after the elongation.

2. The flow diversion apparatus of claim 1, wherein the thin-film stent cover has a thickness between 12 microns and 2 microns.

3. The flow diversion apparatus of claim 1, wherein the fenestrations have a pore size of 300 microns prior to the elongating and a pore size of 200 microns subsequent to the elongating, or a pore size of 500 microns prior to the elongating and a pore size of 400 microns subsequent the elongating.

4. The flow diversion apparatus of claim 1, wherein the thin-film stent cover has a surface coverage of between 5% and 20% subsequent to the elongating.

5. The flow diversion apparatus of claim 1, wherein the thin-film stent cover comprises at least one super-hydrophilic surface.

6. The flow diversion apparatus of claim 5, wherein the at least one super-hydrophilic surface has a water contact angle of less than 5 degrees.

7. The flow diversion apparatus of claim 5, wherein the at least one super-hydrophilic surface is configured to deter platelet adhesion at a rate of less than 3 parts per $mm^2$ when subjected to platelet rich plasma for 3 or more hours.

8. The flow diversion apparatus of claim 1, further comprising: a collapsible stent; wherein the thin-film stent cover is disposed over the stent.

9. The flow diversion apparatus of claim 1, wherein the thin-film stent cover is capable of accommodating strain to at least 800% without failure.

10. The flow diversion apparatus of claim 1, wherein the substrate comprises a Si substrate.

11. The flow diversion apparatus of claim 1, wherein the depositing of the metal sacrificial layer comprises depositing a Cu sacrificial layer by e-beam evaporation.

12. The flow diversion apparatus of claim 1, further comprising depositing a $SiO_2$ barrier layer by plasma-enhanced chemical vapor deposition (PECVD) on the metal sacrificial layer prior to the depositing of the Nitinol.

13. The flow diversion apparatus of claim 1, wherein the depositing of the Nitinol comprises depositing the Nitinol by a direct current (DC) sputtering process.

14. The flow diversion apparatus of claim 1, wherein the depositing of the Nitinol comprises a hot-target sputter deposition.

15. The flow diversion apparatus of claim 1, wherein the crystallizing comprises placing the thin-film Nitinol at 500° C. for 120 minutes.

16. The flow diversion apparatus of claim 1, wherein each fenestration of the plurality of fenestrations has a pore size of 150 microns prior to elongation.

17. The flow diversion apparatus of claim 1, wherein the thin-film stent cover is capable of elongating to at least 400% without substantial deformation.

* * * * *